(12) United States Patent
Van Eenennaam et al.

(10) Patent No.: US 10,107,821 B2
(45) Date of Patent: Oct. 23, 2018

(54) PROLIFERATION-INDUCING LIGAND (APRIL)-BINDING PEPTIDES

(71) Applicant: ADURO BIOTECH HOLDINGS, EUROPE B.V., Oss (NL)

(72) Inventors: Hans Van Eenennaam, Nijmegen (NL); Andrea Van Elsas, Oss (NL); Lilian Driessen, Baarlo (NL); Jan Paul Medema, Amsterdam (NL)

(73) Assignee: ADURO BIOTECH HOLDINGS, EUROPE B.V., Oss (NL)

( * ) Notice: Subject to any disclaimer, the term of this patent is extended or adjusted under 35 U.S.C. 154(b) by 149 days.

(21) Appl. No.: 14/916,962

(22) PCT Filed: Sep. 5, 2014

(86) PCT No.: PCT/NL2014/050612
§ 371 (c)(1),
(2) Date: Mar. 4, 2016

(87) PCT Pub. No.: WO2015/034364
PCT Pub. Date: Mar. 12, 2015

(65) Prior Publication Data
US 2016/0202267 A1   Jul. 14, 2016

(30) Foreign Application Priority Data
Sep. 6, 2013   (NL) .................................. 2011406

(51) Int. Cl.
*G01N 33/68* (2006.01)
*C07K 16/24* (2006.01)
*C07K 16/28* (2006.01)

(52) U.S. Cl.
CPC ....... *G01N 33/6854* (2013.01); *C07K 16/241* (2013.01); *C07K 16/2875* (2013.01); *G01N 33/6863* (2013.01); *C07K 2317/565* (2013.01); *G01N 2333/525* (2013.01)

(58) Field of Classification Search
CPC .......... G01N 33/6854; G01N 33/6863; G01N 2333/525; C07K 16/241; C07K 16/2875; C07K 2317/565
See application file for complete search history.

(56) References Cited

U.S. PATENT DOCUMENTS

| | | |
|---|---|---|
| 7,276,241 B2 | 10/2007 | Schneider et al. |
| 8,105,603 B2 | 1/2012 | Kelley et al. |
| 8,895,705 B2 | 11/2014 | Medema et al. |
| 2002/0086018 A1* | 7/2002 | Theill .............. C07K 14/70575 424/146.1 |

FOREIGN PATENT DOCUMENTS

| | | |
|---|---|---|
| WO | 199912965 A2 | 3/1999 |
| WO | 0160397 A1 | 8/2001 |
| WO | 2007039489 A1 | 4/2007 |
| WO | 2010100056 A2 | 9/2010 |

OTHER PUBLICATIONS

Paul, WE. Fundamental Immunology, 3rd ed. Raven Press, NY, Chap. 9, pp. 292-295, 1993.*
Rudikoff S. et al. Proc. Natl. Acad. Sci. USA, 79:1979-1983, 1982.*
Colman, PM. Research in Immunology, Elsevier, NY, 145(1):33-36, 1994.*
International Search Report dated Jan. 27, 2015 in PCT/NL2014/050612 (5 pages).
Written Opinion dated Jan. 27, 2015 in PCT/NL2014/050612 (8 pages)i.
Li et al., "Repertoire diversification in mice with an IgH-locus-targeted transgene for the rearranged VH domain of a physiologically selected anti-ssDNA antibody", Mol Immunol. Aug. 2005;42(12):1475-84. Epub Mar. 5, 2005. Abstract Only.
Guadagnoli et al., "Development and characterization of APRIL antagonistic monoclonal antibodies for treatment of B-cell lymphomas", Blood. Jun. 23, 2011;117(25):6856-65. doi: 10.1182/blood-2011-01-330852. Epub May 4, 2011.
Hardenberg et al., Specific TLR ligands regulate APRIL secretion by dendritic cells in a PKR-dependent manner. Eur J Immunol. Oct. 2007;37(10):2900-2911.
Liu and Hou, Immune Thrombocytopenia and B-Cell-Activating Factor/A Proliferation-Inducing Ligand. Semin Hematol. Jan. 2013;50 Suppl 1:S89-S99.
Sakurai et al., TACI regulates IgA production by APRIL in collaboration with HSPG. Blood. Apr. 1, 2007;109(7):2961-2967.
Treamtrakanpon et al., APRIL, a proliferation-inducing ligand, as a potential marker of lupus nephritis. Arthritis Res Ther. Nov. 21, 2012;14(6):R252.
Wang et al., APRIL Induces Tumorigenesis and Metastasis of Colorectal Cancer Cells via Activation of the PI3K/Akt Pathway. PLoS One. 2013;8(1):e55298.

* cited by examiner

*Primary Examiner* — Robert S Landsman
(74) *Attorney, Agent, or Firm* — Acuity Law Group, PC; Michael A. Whittaker

(57) ABSTRACT

The invention relates to a method for obtaining APRIL-binding peptides. With this method APRIL-binding peptides may be obtained and/or selected. Further aspects of the invention relate to a cell comprising a nucleotide sequence coding for an APRIL-binding peptide according to the invention, a process for producing an APRIL-binding peptide and the APRIL-binding peptide obtainable in the production process and/or the selection method. In view of the possible utility of the APRIL-binding peptides according to the invention, further aspects of the invention relate to diagnostic uses of an APRIL binding peptide of the invention.

3 Claims, 5 Drawing Sheets
Specification includes a Sequence Listing.

```
                        SEQUENCE LISTING

<160> NUMBER OF SEQ ID NOS: 50

<210> SEQ ID NO 1
<211> LENGTH: 345
<212> TYPE: DNA
<213> ORGANISM: Mus musculus
<220> FEATURE:
<221> NAME/KEY: source
<222> LOCATION: 1..345
<223> OTHER INFORMATION: /mol_type="unassigned DNA"
      /organism="Mus musculus"

<400> SEQUENCE: 1
caggtgcagc tgaaggagtc aggacctggc ctggtggcgc cctcacagag cctgtccatc      60
acatgcaccg tctcagggtt ctcattaacc ggctatggta taaactgggt tcgccagcct     120
ccaggaaagg gtctggagtg gctgggagtg atatggggtg atggaagcac agagtataat     180
tcagctctca aatccagact gagcatcagc aaggacaagt ccaagagcca agttttctta     240
aaaatgaaca gtctgcaaac tgatgacaca gccaggtact actgtgccag agatgatgat     300
gttatggact actggggtca aggaacctca gtcaccgtct cctca                     345

<210> SEQ ID NO 2
<211> LENGTH: 323
<212> TYPE: DNA
<213> ORGANISM: Mus musculus
<220> FEATURE:
<221> NAME/KEY: source
<222> LOCATION: 1..323
<223> OTHER INFORMATION: /mol_type="unassigned DNA"
      /organism="Mus musculus"

<400> SEQUENCE: 2
agtattgtga tgacccagac tcccaaattc ctgcttgttt cagcaggaga cagggttacc      60
ataacctgca aggccggtca gagtgtgact aatgatgtag cttggtacca acagaagcca     120
```

```
gggcagtctc ctaaattgct gatatactat gcatccaatc gcttcactgg agtccctgat    180
cgcttcactg gcagtggata tgggacggat ttcactttcg ccatcagcac tgtgcaggct    240
gaagacctgg cagtttattt ctgtcagcag gattatagct ctccgtggac gttcggtgga    300
ggcaccaagc tggaaatcaa acg                                            323
```

```
<210> SEQ ID NO 3
<211> LENGTH: 115
<212> TYPE: PRT
<213> ORGANISM: Mus musculus

<400> SEQUENCE: 3
```

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
            20                  25                  30

Gly Val Asn Trp Val Arg Gln Pro Pro Gly Lys Gly Leu Glu Trp Leu
        35                  40                  45

Gly Val Ile Trp Gly Asp Gly Ser Thr Glu Tyr Asn Ser Ala Leu Lys
    50                  55                  60

Ser Arg Leu Ser Ile Ser Lys Asp Lys Ser Lys Ser Gln Val Phe Leu
65                  70                  75                  80

Lys Met Asn Ser Leu Gln Thr Asp Asp Thr Ala Arg Tyr Tyr Cys Ala
                85                  90                  95

Arg Asp Asp Asp Val Met Asp Tyr Trp Gly Gln Gly Thr Ser Val Thr
            100                 105                 110

Val Ser Ser
        115

```
<210> SEQ ID NO 4
<211> LENGTH: 107
<212> TYPE: PRT
<213> ORGANISM: Mus musculus

<400> SEQUENCE: 4
```

Ser Ile Val Met Thr Gln Thr Pro Lys Phe Leu Leu Val Ser Ala Gly
1               5                   10                  15

Asp Arg Val Thr Ile Thr Cys Lys Ala Gly Gln Ser Val Thr Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Phe Thr Gly Val Pro Asp Arg Phe Thr Gly
    50                  55                  60

Ser Gly Tyr Gly Thr Asp Phe Thr Phe Ala Ile Ser Thr Val Gln Ala
65                  70                  75                  80

Glu Asp Leu Ala Val Tyr Phe Cys Gln Gln Asp Tyr Ser Ser Pro Trp
                85                  90                  95

Thr Phe Gly Gly Gly Thr Lys Leu Glu Ile Lys
            100                 105

```
<210> SEQ ID NO 5
<211> LENGTH: 5
<212> TYPE: PRT
<213> ORGANISM: Mus musculus

<400> SEQUENCE: 5
```

Gly Tyr Gly Val Asn

<210> SEQ ID NO 6
<211> LENGTH: 16
<212> TYPE: PRT
<213> ORGANISM: Mus musculus

<400> SEQUENCE: 6

Val Ile Trp Gly Asp Gly Ser Thr Glu Tyr Asn Ser Ala Leu Lys Ser
1               5                   10                  15

<210> SEQ ID NO 7
<211> LENGTH: 7
<212> TYPE: PRT
<213> ORGANISM: Mus musculus

<400> SEQUENCE: 7

Asp Asp Asp Val Met Asp Tyr
1               5

<210> SEQ ID NO 8
<211> LENGTH: 11
<212> TYPE: PRT
<213> ORGANISM: Mus musculus

<400> SEQUENCE: 8

Lys Ala Gly Gln Ser Val Thr Asn Asp Val Ala
1               5                   10

<210> SEQ ID NO 9
<211> LENGTH: 7
<212> TYPE: PRT
<213> ORGANISM: Mus musculus

<400> SEQUENCE: 9

Tyr Ala Ser Asn Arg Phe Thr
1               5

<210> SEQ ID NO 10
<211> LENGTH: 9
<212> TYPE: PRT
<213> ORGANISM: Mus musculus

<400> SEQUENCE: 10

Gln Gln Asp Tyr Ser Ser Pro Trp Thr
1               5

<210> SEQ ID NO 11
<211> LENGTH: 366
<212> TYPE: DNA
<213> ORGANISM: Mus musculus
<220> FEATURE:
<221> NAME/KEY: source
<222> LOCATION: 1..366
<223> OTHER INFORMATION: /mol_type="unassigned DNA"
      /organism="Mus musculus"

<400> SEQUENCE: 11
caggagcagc tgaaggagtc aggacctggc ctggtggcgc cctcacagag cctgtccatc    60
acttgcactg tctctggggtt ttcattaacc agctatggtg tacattgggt tcgccagcct   120
ccaggaaagg gtctggagtg gctgggagtt atatgggctg gtggaagcac aaattataac   180
tcggctctca tgtccagact gagcatcagt agagacaact ccaagagcca agttttctta   240
aaaatgaaca gtctgcaaac tgatgacaca gccatgtact actgtgccag agagggcttt   300

```
gacacctcgg gcttctacta tgctatggac tactggggtc aaggaacctc agtcaccgtc    360
tcctca                                                               366
```

<210> SEQ ID NO 12
<211> LENGTH: 323
<212> TYPE: DNA
<213> ORGANISM: Mus musculus
<220> FEATURE:
<221> NAME/KEY: source
<222> LOCATION: 1..323
<223> OTHER INFORMATION: /mol_type="unassigned DNA"
      /organism="Mus musculus"

<400> SEQUENCE: 12

```
gatatccaga tgacacagac tacatcctcc ctgtctgcct ctctgggaga cagagtcacc     60
atcagttgca gggcaggtca ggccattagc aattatttaa actggtatca gcagaaacca    120
ggtggaactg ttaaactcct gatctactac acatcaaaat tacactcagg agtcccatca    180
aggttcagtg gcagtggctc tggaacagat tattctctca ccattagcaa cctgaacaa     240 gaagatattg ccacttactt ttgccaacag ggttatacgc ttccgtacac gttcggaggg    300
gggaccaagc tggaaataaa acg                                            323
```

<210> SEQ ID NO 13
<211> LENGTH: 122
<212> TYPE: PRT
<213> ORGANISM: Mus musculus

<400> SEQUENCE: 13

```
Gln Glu Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Gly Val Ile Trp Ala Gly Gly Ser Thr Asn Tyr Asn Ser Ala Leu Met
    50                  55                  60

Ser Arg Leu Ser Ile Ser Arg Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Glu Gly Leu Asp Thr Ser Gly Phe Tyr Tyr Ala Met Asp Tyr Trp
            100                 105                 110

Gly Gln Gly Thr Ser Val Thr Val Ser Ser
        115                 120
```

<210> SEQ ID NO 14
<211> LENGTH: 107
<212> TYPE: PRT
<213> ORGANISM: Mus musculus

<400> SEQUENCE: 14

```
Asp Ile Gln Met Thr Gln Thr Thr Ser Ser Leu Ser Ala Ser Leu Gly
1               5                   10                  15

Asp Arg Val Thr Ile Ser Cys Arg Ala Gly Gln Ala Ile Ser Asn Tyr
            20                  25                  30

Leu Asn Trp Tyr Gln Gln Lys Pro Gly Gly Thr Val Lys Leu Leu Ile
        35                  40                  45
```

```
Tyr Tyr Thr Ser Lys Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Tyr Thr Leu Pro Tyr
                85                  90                  95

Thr Phe Gly Gly Gly Thr Lys Leu Glu Ile Lys
            100                 105
```

<210> SEQ ID NO 15
<211> LENGTH: 5
<212> TYPE: PRT
<213> ORGANISM: Mus musculus

<400> SEQUENCE: 15

```
Ser Tyr Gly Val His
1               5
```

<210> SEQ ID NO 16
<211> LENGTH: 16
<212> TYPE: PRT
<213> ORGANISM: Mus musculus

<400> SEQUENCE: 16

```
Val Ile Trp Ala Gly Gly Ser Thr Asn Tyr Asn Ser Ala Leu Met Ser
1               5                   10                  15
```

<210> SEQ ID NO 17
<211> LENGTH: 14
<212> TYPE: PRT
<213> ORGANISM: Mus musculus

<400> SEQUENCE: 17

```
Glu Gly Leu Asp Thr Ser Gly Phe Tyr Tyr Ala Met Asp Tyr
1               5                   10
```

<210> SEQ ID NO 18
<211> LENGTH: 11
<212> TYPE: PRT
<213> ORGANISM: Mus musculus

<400> SEQUENCE: 18

```
Arg Ala Gly Gln Ala Ile Ser Asn Tyr Leu Asn
1               5                   10
```

<210> SEQ ID NO 19
<211> LENGTH: 7
<212> TYPE: PRT
<213> ORGANISM: Mus musculus

<400> SEQUENCE: 19

```
Tyr Thr Ser Lys Leu His Ser
1               5
```

<210> SEQ ID NO 20
<211> LENGTH: 9
<212> TYPE: PRT
<213> ORGANISM: Mus musculus

<400> SEQUENCE: 20

```
Gln Gln Gly Tyr Thr Leu Pro Tyr Thr
1               5
```

-continued

<210> SEQ ID NO 21
<211> LENGTH: 345
<212> TYPE: DNA
<213> ORGANISM: Mus musculus
<220> FEATURE:
<221> NAME/KEY: source
<222> LOCATION: 1..345
<223> OTHER INFORMATION: /mol_type="unassigned DNA"
    /organism="Mus musculus"

<400> SEQUENCE: 21

```
caggtgcagt tgaaggagtc aggacctggc ctggtggcgc cctcacagag cctgtccatc      60
acatgcaccg tctcagggtt ctcattaacc ggctatggtg taaactgggt tcgccagcct     120
ccaggaaagg gtctggagtg gctgggagtg atatggggtg atggaagcac agagtataat     180
tcagctctca atccagact gagcatcagc aaggacaagt ccaagagcca agttttctta     240
aaaatgaaca gtctgcaaac tgatgacaca gccaggtact actgtgccag agatgatgat     300
gttatggact actggggtca aggaacctca gtcaccgtct cctca                     345
```

<210> SEQ ID NO 22
<211> LENGTH: 323
<212> TYPE: DNA
<213> ORGANISM: Mus musculus
<220> FEATURE:
<221> NAME/KEY: source
<222> LOCATION: 1..323
<223> OTHER INFORMATION: /mol_type="unassigned DNA"
    /organism="Mus musculus"

<400> SEQUENCE: 22

```
agtattgtga tgacccagac tcccaaattc ctgcttgttt cagcaggaga cagcattacc      60
ataacctgca aggccgatca gagtgtgagt agtgatgtag cttggtacca acagaaggca     120
gggcagtctc ctaaattgct gatatactat gcatccaatc gctacactgg agtccctgat     180
cgcttcactg gcagtggata tgggacggat ttcactttcg ccatcagctc tgtgcaggct     240
gaagacctgg cagtttattt ctgtcagcag gattatagct ctccgtggac gttcggtgga     300
ggcaccaagc tggaaatcaa acg                                              323
```

<210> SEQ ID NO 23
<211> LENGTH: 115
<212> TYPE: PRT
<213> ORGANISM: Mus musculus

<400> SEQUENCE: 23

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
            20                  25                  30

Gly Val Asn Trp Val Arg Gln Pro Pro Gly Lys Gly Leu Glu Trp Leu
        35                  40                  45

Gly Val Ile Trp Gly Asp Gly Ser Thr Glu Tyr Asn Ser Ala Leu Lys
    50                  55                  60

Ser Arg Leu Ser Ile Ser Lys Asp Lys Ser Lys Ser Gln Val Phe Leu
65                  70                  75                  80

Lys Met Asn Ser Leu Gln Thr Asp Asp Thr Ala Arg Tyr Tyr Cys Ala
                85                  90                  95

Arg Asp Asp Asp Val Met Asp Tyr Trp Gly Gln Gly Thr Ser Val Thr
            100                 105                 110

Val Ser Ser
```

<210> SEQ ID NO 24
<211> LENGTH: 107
<212> TYPE: PRT
<213> ORGANISM: Mus musculus

<400> SEQUENCE: 24

Ser Ile Val Met Thr Gln Thr Pro Lys Phe Leu Leu Val Ser Ala Gly
1               5                   10                  15

Asp Ser Ile Thr Ile Thr Cys Lys Ala Asp Gln Ser Val Ser Ser Asp
            20                  25                  30

Val Ala Trp Tyr Gln Gln Lys Ala Gly Gln Ser Pro Lys Leu Leu Ile
        35                  40                  45

Tyr Tyr Ala Ser Asn Arg Tyr Thr Gly Val Pro Asp Arg Phe Thr Gly
50                  55                  60

Ser Gly Tyr Gly Thr Asp Phe Thr Phe Ala Ile Ser Ser Val Gln Ala
65                  70                  75                  80

Glu Asp Leu Ala Val Tyr Phe Cys Gln Gln Asp Tyr Ser Ser Pro Trp
                85                  90                  95

Thr Phe Gly Gly Gly Thr Lys Leu Glu Ile Lys
            100                 105

<210> SEQ ID NO 25
<211> LENGTH: 5
<212> TYPE: PRT
<213> ORGANISM: Mus musculus

<400> SEQUENCE: 25

Gly Tyr Gly Val Asn
1               5

<210> SEQ ID NO 26
<211> LENGTH: 16
<212> TYPE: PRT
<213> ORGANISM: Mus musculus

<400> SEQUENCE: 26

Val Ile Trp Gly Asp Gly Ser Thr Glu Tyr Asn Ser Ala Leu Lys Ser
1               5                   10                  15

<210> SEQ ID NO 27
<211> LENGTH: 7
<212> TYPE: PRT
<213> ORGANISM: Mus musculus

<400> SEQUENCE: 27

Asp Asp Asp Val Met Asp Tyr
1               5

<210> SEQ ID NO 28
<211> LENGTH: 11
<212> TYPE: PRT
<213> ORGANISM: Mus musculus

<400> SEQUENCE: 28

Lys Ala Asp Gln Ser Val Ser Ser Asp Val Ala
1               5                   10

<210> SEQ ID NO 29
<211> LENGTH: 7
<212> TYPE: PRT

<213> ORGANISM: Mus musculus

<400> SEQUENCE: 29

Tyr Ala Ser Asn Arg Tyr Thr
1               5

<210> SEQ ID NO 30
<211> LENGTH: 9
<212> TYPE: PRT
<213> ORGANISM: Mus musculus

<400> SEQUENCE: 30

Gln Gln Asp Tyr Ser Ser Pro Trp Thr
1               5

<210> SEQ ID NO 31
<211> LENGTH: 354
<212> TYPE: DNA
<213> ORGANISM: Mus musculus
<220> FEATURE:
<221> NAME/KEY: source
<222> LOCATION: 1..354
<223> OTHER INFORMATION: /mol_type="unassigned DNA"
      /organism="Mus musculus"

<400> SEQUENCE: 31

```
caggtgcagc tgaaggagtc aggacctggc ctggtagcac cctcacagag cctgtccatc      60
acatgcactg tctctgggtt ctcattatcc agatatagtg tacactgggt tcgccagcct    120
ccaggaaagg gtctggagtg gctgggaatg atatggggtg gtggaagcac agactataat    180
tcagctctca aatccagact gagcatcagc aaggacaact ccaagaggca agttttctta    240
aaaatgaaca gtctgcaaac tgatgacaca gccatttact actgtgccag atctaactgg    300
gagatctatg ctttggacta ttggggtcaa ggaacctcag tcaccgtctc ctca          354
```

<210> SEQ ID NO 32
<211> LENGTH: 335
<212> TYPE: DNA
<213> ORGANISM: Mus musculus
<220> FEATURE:
<221> NAME/KEY: source
<222> LOCATION: 1..335
<223> OTHER INFORMATION: /mol_type="unassigned DNA"
      /organism="Mus musculus"

<400> SEQUENCE: 32

```
gacattgtgc tgacccaatc tccagcttct ttggctgtgt ctctagggca gagggccacc     60
atctcctgca aggccagcca agtattgat tatgatggtg ataattatat gaactggtac    120
caacagaaac caggacagcc acccaaactc ctcatctatg ttgcatccag tctagaatct    180
gggatcccag ccaggtttag tggcagtggg tctgggacag acttcaccct caacatccat    240
cctgtggagg aggaggatgc tgcaacctat tactgtcagc aaagtaatgt ggagccgtac    300
acgttcggag gggggaccaa gctggaaata aaacg                               335
```

<210> SEQ ID NO 33
<211> LENGTH: 118
<212> TYPE: PRT
<213> ORGANISM: Mus musculus

<400> SEQUENCE: 33

Gln Val Gln Leu Lys Glu Ser Gly Pro Gly Leu Val Ala Pro Ser Gln
1               5                   10                  15

```
Ser Leu Ser Ile Thr Cys Thr Val Ser Gly Phe Ser Leu Ser Arg Tyr
                20                  25                  30

Ser Val His Trp Val Arg Gln Pro Gly Lys Gly Leu Glu Trp Leu
        35                  40                  45

Gly Met Ile Trp Gly Gly Ser Thr Asp Tyr Asn Ser Ala Leu Lys
    50                  55                  60

Ser Arg Leu Ser Ile Ser Lys Asp Asn Ser Lys Arg Gln Val Phe Leu
65                  70                  75                  80

Lys Met Asn Ser Leu Gln Thr Asp Thr Ala Ile Tyr Tyr Cys Ala
                85                  90                  95

Arg Ser Asn Trp Glu Ile Tyr Ala Leu Asp Tyr Trp Gly Gln Gly Thr
                100                 105                 110

Ser Val Thr Val Ser Ser
            115

<210> SEQ ID NO 34
<211> LENGTH: 111
<212> TYPE: PRT
<213> ORGANISM: Mus musculus

<400> SEQUENCE: 34

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Ile Asp Tyr Asp
                20                  25                  30

Gly Asp Asn Tyr Met Asn Trp Tyr Gln Gln Lys Pro Gly Gln Pro Pro
            35                  40                  45

Lys Leu Leu Ile Tyr Val Ala Ser Ser Leu Glu Ser Gly Ile Pro Ala
        50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Val Glu Pro Tyr Thr Phe Gly Gly Gly Thr Lys Leu Glu Ile Lys
                100                 105                 110

<210> SEQ ID NO 35
<211> LENGTH: 5
<212> TYPE: PRT
<213> ORGANISM: Mus musculus

<400> SEQUENCE: 35

Arg Tyr Ser Val His
1               5

<210> SEQ ID NO 36
<211> LENGTH: 16
<212> TYPE: PRT
<213> ORGANISM: Mus musculus

<400> SEQUENCE: 36

Met Ile Trp Gly Gly Gly Ser Thr Asp Tyr Asn Ser Ala Leu Lys Ser
1               5                   10                  15

<210> SEQ ID NO 37
<211> LENGTH: 10
<212> TYPE: PRT
<213> ORGANISM: Mus musculus

<400> SEQUENCE: 37
```

Ser Asn Trp Glu Ile Tyr Ala Leu Asp Tyr
1               5                   10

<210> SEQ ID NO 38
<211> LENGTH: 15
<212> TYPE: PRT
<213> ORGANISM: Mus musculus

<400> SEQUENCE: 38

Lys Ala Ser Gln Ser Ile Asp Tyr Asp Gly Asp Asn Tyr Met Asn
1               5                   10                  15

<210> SEQ ID NO 39
<211> LENGTH: 7
<212> TYPE: PRT
<213> ORGANISM: Mus musculus

<400> SEQUENCE: 39

Val Ala Ser Ser Leu Glu Ser
1               5

<210> SEQ ID NO 40
<211> LENGTH: 9
<212> TYPE: PRT
<213> ORGANISM: Mus musculus

<400> SEQUENCE: 40

Gln Gln Ser Asn Val Glu Pro Tyr Thr
1               5

<210> SEQ ID NO 41
<211> LENGTH: 354
<212> TYPE: DNA
<213> ORGANISM: Mus musculus
<220> FEATURE:
<221> NAME/KEY: source
<222> LOCATION: 1..354
<223> OTHER INFORMATION: /mol_type="unassigned DNA"
      /organism="Mus musculus"

<400> SEQUENCE: 41
caggtgcagc tgaaggagtc aggacctggc ctggtggcac cctcacagag cctgtccatc        60
acatgcactg tctctgggtt ctcattatcc agatatagta tacactgggt tcgccagcct       120
ccaagaaagg gtctggagtg gctgggaatg atatgggtg gtggaagcac agactataat       180
tcagctctca aatccagact gagcatcaac aaggacaact ccaagaggca agttttctta       240
aaaatgcaca gtctgcaaac tgatgacaca gccatctact actgtgccag atctaactgg       300
gagatctatg ctatggacta ctggggtcaa ggaacctcag tcaccgtctc ctca            354

<210> SEQ ID NO 42
<211> LENGTH: 335
<212> TYPE: DNA
<213> ORGANISM: Mus musculus
<220> FEATURE:
<221> NAME/KEY: source
<222> LOCATION: 1..335
<223> OTHER INFORMATION: /mol_type="unassigned DNA"
      /organism="Mus musculus"

<400> SEQUENCE: 42
gacattgtgc tgacccaatc tccaccttct ttggctgtgt ctctagggca gagggccacc        60
atctcctgca aggccagcca agtattgat tatgatggtg atcgttatat gaactggtac       120

```
caacagaaac caggacagcc acccaaactc ctcatctatg ttgcatccaa tctagaatct    180
gggatcccag ccaggtttag tggcagtggg tctgggacag acttcaccct caacatccat    240
cctgtggagg aggaggatgc tgcaacctat tactgtcagc aaagtcatga ggagccgcac    300
acgttcggag gggggaccaa gctggaaata aaacg                               335
```

<210> SEQ ID NO 43
<211> LENGTH: 118
<212> TYPE: PRT
<213> ORGANISM: Mus musculus
<400> SEQUENCE: 43

```
Gln Val Gln Leu Lys Glu Ser Gly Pro Gly Leu Val Ala Pro Ser Gln
  1               5                  10                  15

Ser Leu Ser Ile Thr Cys Thr Val Ser Gly Phe Ser Leu Ser Arg Tyr
             20                  25                  30

Ser Ile His Trp Val Arg Gln Pro Pro Arg Lys Gly Leu Glu Trp Leu
         35                  40                  45

Gly Met Ile Trp Gly Gly Gly Ser Thr Asp Tyr Asn Ser Ala Leu Lys
     50                  55                  60

Ser Arg Leu Ser Ile Asn Lys Asp Asn Ser Lys Arg Gln Val Phe Leu
 65                  70                  75                  80

Lys Met His Ser Leu Gln Thr Asp Asp Thr Ala Ile Tyr Tyr Cys Ala
                 85                  90                  95

Arg Ser Asn Trp Glu Ile Tyr Ala Met Asp Tyr Trp Gly Gln Gly Thr
            100                 105                 110

Ser Val Thr Val Ser Ser
        115
```

<210> SEQ ID NO 44
<211> LENGTH: 111
<212> TYPE: PRT
<213> ORGANISM: Mus musculus
<400> SEQUENCE: 44

```
Asp Ile Val Leu Thr Gln Ser Pro Pro Ser Leu Ala Val Ser Leu Gly
  1               5                  10                  15

Gln Arg Ala Thr Ile Ser Cys Lys Ala Ser Gln Ser Ile Asp Tyr Asp
             20                  25                  30

Gly Asp Arg Tyr Met Asn Trp Tyr Gln Gln Lys Pro Gly Gln Pro Pro
         35                  40                  45

Lys Leu Leu Ile Tyr Val Ala Ser Asn Leu Glu Ser Gly Ile Pro Ala
     50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln Gln Ser His
                 85                  90                  95

Glu Glu Pro His Thr Phe Gly Gly Gly Thr Lys Leu Glu Ile Lys
            100                 105                 110
```

<210> SEQ ID NO 45
<211> LENGTH: 5
<212> TYPE: PRT
<213> ORGANISM: Mus musculus
<400> SEQUENCE: 45

```
Arg Tyr Ser Ile His
  1               5
```

```
<210> SEQ ID NO 46
<211> LENGTH: 16
<212> TYPE: PRT
<213> ORGANISM: Mus musculus

<400> SEQUENCE: 46

Met Ile Trp Gly Gly Gly Ser Thr Asp Tyr Asn Ser Ala Leu Lys Ser
1               5                   10                  15

<210> SEQ ID NO 47
<211> LENGTH: 10
<212> TYPE: PRT
<213> ORGANISM: Mus musculus

<400> SEQUENCE: 47

Ser Asn Trp Glu Ile Tyr Ala Met Asp Tyr
1               5                   10

<210> SEQ ID NO 48
<211> LENGTH: 15
<212> TYPE: PRT
<213> ORGANISM: Mus musculus

<400> SEQUENCE: 48

Lys Ala Ser Gln Ser Ile Asp Tyr Asp Gly Asp Arg Tyr Met Asn
1               5                   10                  15

<210> SEQ ID NO 49
<211> LENGTH: 7
<212> TYPE: PRT
<213> ORGANISM: Mus musculus

<400> SEQUENCE: 49

Val Ala Ser Asn Leu Glu Ser
1               5

<210> SEQ ID NO 50
<211> LENGTH: 9
<212> TYPE: PRT
<213> ORGANISM: Mus musculus

<400> SEQUENCE: 50

Gln Gln Ser His Glu Glu Pro His Thr
1               5
```

PROLIFERATION-INDUCING LIGAND (APRIL)-BINDING PEPTIDES

FIELD OF THE INVENTION

The present invention relates to the field of human and veterinary medicine, including medical/veterinary diagnosis and medical/veterinary research. More specifically the present invention relates to APRIL-binding peptides, including monoclonal antibodies, suitable for use in this or other fields.

BACKGROUND

APRIL is expressed as a type-II transmembrane protein, but unlike most other TNF family members it is mainly processed as a secreted protein and cleaved in the Golgi apparatus where it is cleaved by a furin convertase to release a soluble active form (Lopez-Fraga et al., 2001, *EMBO Rep* 2:945-51). APRIL assembles as a non-covalently linked homo-trimer with similar structural homology in protein fold to a number of other TNF family ligands (Wallweber et al., 2004, *Mol Biol* 343, 283-90). APRIL binds two TNF receptors: B cell maturation antigen (BCMA) and transmembrane activator and calcium modulator and cyclophilin ligand interactor (TACI) (reviewed in Kimberley et al., 2009, *J Cell Physiol.* 218(1):1-8). In addition, APRIL has recently been shown to bind heparan sulphate proteoglycans (HSPGs) (Hendriks et al., 2005, *Cell Death Differ* 12, 637-48). APRIL has been shown to have a role in B cell signalling and drive both proliferation and survival of human and murine B cells in-vitro (reviewed in Kimberley et al., 2009, *J Cell Physiol.* 218(1):1-8).

APRIL is predominantly expressed by immune cell subsets such as monocytes, macrophages, dendritic cells, neutrophils, B-cells, and T-cells, many of which also express BAFF. In addition, APRIL can be expressed by non-immune cells such as osteoclasts, epithelial cells and a variety of tumour tissues (reviewed in Kimberley et al., 2009, *J Cell Physiol.* 218(1):1-8). In fact, APRIL was originally identified based on its expression in cancer cells (Hahne et al., 1998, *J Exp Med* 188, 1185-90). High expression levels of APRIL mRNA were found in a panel of tumour cell lines as well as human primary tumours such as colon, and a lymphoid carcinoma.

A retrospective study under 95 Chronic Lymphocytic Leukaemia (CLL) CLL patients showed increased levels of APRIL in serum, which correlated with disease progression and overall patient survival, with a poorer prognosis for patients with high APRIL serum levels (Planelles et al., 2007, *Haematologica* 92, 1284-5). Similarly, (increased levels of) APRIL was shown to be expressed in Hodgkin's lymphoma, Non-Hodgkin's lymphoma (NHL) and Multiple Myeloma (MM) (reviewed in Kimberley et al., 2009, *J Cell Physiol.* 218(1):1-8). A retrospective study in DLBCL patients (NHL) showed that high APRIL expression in cancer lesions correlated with a poor survival rate (Schwaller et al., 2007, *Blood* 109, 331-8). Recently, APRIL serum levels in serum from patients suffering from colorectal cancer were shown to have a positive diagnostic value (Ding et al., 2013, Clin. Biochemistry, http://dx.doi.org/10.1016/j. clinbiochem.2013.06.008).

Due to its role in B cell biology APRIL also plays a role in many autoimmune diseases. Increased serum levels of APRIL have been reported in many SLE patients (Koyama et al., 2005, *Ann Rheum Dis* 64, 1065-7). A retrospective analysis revealed that APRIL serum levels tended to correlate with anti-dsDNA antibody titres. Also in the synovial fluid of patients with inflammatory arthritis significantly increased APRIL levels as compared with those with patients suffering from non-inflammatory arthritis such as osteoarthritis were detected (Stohl et al., 2006, *Endocr Metab Immune Disord Drug Targets* 6, 351-8; Tan et al., 2003, *Arthritis Rheum* 48, 982-92).

Several studies focused on the presence of APRIL in the sera of patients suffering from a wider range of systemic immune-based rheumatic diseases (now also including Sjögren's syndrome, Reiter's syndrome, psoriatic arthritis, polymyositis, and ankylosing spondylitis) and found significantly increased APRIL levels in these patients, suggesting an important role for APRIL in these diseases as well (Jonsson et al., 1986, *Scand J Rheumatol Suppl* 61, 166-9; Roschke et al., 2002, *J Immunol* 169, 4314-21). In addition, increased APRIL serum levels were detected in serum from patients suffering atopic dermatitis (Matsushita et al., 2007, Exp. Dermatology 17, 197-202). Also, serum APRIL levels are elevated in sepsis and predict mortality in critically ill patients (Roderburg et al., J. Critical Care, 2013, http://dx.doi.org/10.1016/j.jcrc.2012.11.007). Finally, increased APRIL expression has also been linked to Multiple Sclerosis (MS). APRIL expression was found to be increased in the astrocytes of MS sufferers compared with normal controls. This is in line with the described APRIL expression in glioblastomas and in the serum of glioblastoma patients (Deshayes et al., 2004, *Oncogene* 23, 3005-12; Roth et al., 2001, *Cell Death Differ* 8, 403-10).

SUMMARY

With APRIL representing an important marker for diseases, such as, but not limited to autoimmune diseases, inflammatory diseases and malignancies, detection of APRIL in the serum of human subjects is important. Current available assays involve the use of (ill-defined and limited available) polyclonal antibodies (Planelles et al., 2007, *Haematologica* 92, 1284-5), do not reproduce reported APRIL levels in serum and/or the quantification of APRIL is heavily impacted by the presence of human serum (BioLegend, see Example 1), require an Immunoglobulin-absorption step prior to assessment of APRIL protein levels (Matsushita et al., 2007, Exp. Dermatology 17, 197-202) or demonstrate limited detection limits (R&D systems). In view of the shortcomings of the prior art anti-APRIL antibodies, the inventors of the present invention set out to develop methods to identify and obtain APRIL-binding peptides suitable to detect APRIL in the context of a human sample, preferably a blood-derived sample such as a serum sample. In particular methods were designed and developed to select the rarely abundant B-cells that express the antibodies from APRIL immunized mice.

In brief the method of the invention for obtaining APRIL-binding peptides comprises the steps of:
  providing a library of binder peptides;
  selecting APRIL-binding peptides from the library by means of affinity selection using a target peptide immobilized on a solid support, said target peptide comprising a number of APRIL epitopes and an APRIL receptor-binding region of APRIL;
  characterized in that, the target peptide is in interaction with a peptide, the shielding peptide, comprising an APRIL-binding region of an APRIL receptor or of an APRIL-binding equivalent thereof. With this method APRIL-binding peptides may be obtained and/or selected.

The method developed can be exploited broadly and may be used to obtain a broad range of APRIL-binding peptides, such as APRIL-binding antibodies.

Further aspects of the invention relate to an APRIL-binding peptide obtainable with a method according to the invention, a cell comprising a nucleotide sequence coding for an APRIL-binding peptide according to the invention, a process for producing APRIL-binding peptides and the APRIL binding peptides obtainable with this process. In addition the use of an APRIL-binding peptide according to the invention in a diagnostic test, preferably an ex vivo diagnostic test, is also within the scope of the present invention.

BRIEF DESCRIPTION OF THE SEQUENCES

The sequences presented in the sequence listing relate to the amino acid sequences and encoding DNA sequences of the $V_H$ and $V_L$ chains of five immunoglobulins (hAPRIL.130, hAPRIL.132, hAPRIL.133, hAPRIL.135, hAPRIL.138) obtained with the method of the invention. In addition the amino acid sequences of the CDR regions of both the $V_H$ and $V_L$ chains of these immunoglobulins are presented. Table 1 below correlates the sequence IDs to their respective sequence.

TABLE 1

| SEQ ID NO: | Description |
| --- | --- |
| 1 | hAPRIL.130 heavy chain variable region (DNA) |
| 2 | hAPRIL.130 light chain variable region (DNA) |
| 3 | hAPRIL.130 heavy chain variable region (AA) |
| 4 | hAPRIL.130 light chain variable region (AA) |
| 5 | hAPRIL.130 heavy chain CDR1 (AA) |
| 6 | hAPRIL.130 heavy chain CDR2 (AA) |
| 7 | hAPRIL.130 heavy chain CDR3 (AA) |
| 8 | hAPRIL.130 light chain CDR1 (AA) |
| 9 | hAPRIL.130 light chain CDR2 (AA) |
| 10 | hAPRIL.130 light chain CDR3 (AA) |
| 11 | hAPRIL.132 heavy chain variable region (DNA) |
| 12 | hAPRIL.132 light chain variable region (DNA) |
| 13 | hAPRIL.132 heavy chain variable region (AA) |
| 14 | hAPRIL.132 light chain variable region (AA) |
| 15 | hAPRIL.132 heavy chain CDR1 (AA) |
| 16 | hAPRIL.132 heavy chain CDR2 (AA) |
| 17 | hAPRIL.132 heavy chain CDR3 (AA) |
| 18 | hAPRIL.132 light chain CDR1 (AA) |
| 19 | hAPRIL.132 light chain CDR2 (AA) |
| 20 | hAPRIL.132 light chain CDR3 (AA) |
| 21 | hAPRIL.133 heavy chain variable region (DNA) |
| 22 | hAPRIL.133 light chain variable region (DNA) |
| 23 | hAPRIL.133 heavy chain variable region (AA) |
| 24 | hAPRIL.133 light chain variable region (AA) |
| 25 | hAPRIL.133 heavy chain CDR1 (AA) |
| 26 | hAPRIL.133 heavy chain CDR2 (AA) |
| 27 | hAPRIL.133 heavy chain CDR3 (AA) |
| 28 | hAPRIL.133 light chain CDR1 (AA) |
| 29 | hAPRIL.133 light chain CDR2 (AA) |
| 30 | hAPRIL.133 light chain CDR3 (AA) |
| 31 | hAPRIL.135 heavy chain variable region (DNA) |
| 32 | hAPRIL.135 light chain variable region (DNA) |
| 33 | hAPRIL.135 heavy chain variable region (AA) |
| 34 | hAPRIL.135 light chain variable region (AA) |
| 35 | hAPRIL.135 heavy chain CDR1 (AA) |
| 36 | hAPRIL.135 heavy chain CDR2 (AA) |
| 37 | hAPRIL.135 heavy chain CDR3 (AA) |
| 38 | hAPRIL.135 light chain CDR1 (AA) |
| 39 | hAPRIL.135 light chain CDR2 (AA) |
| 40 | hAPRIL.135 light chain CDR3 (AA) |
| 41 | hAPRIL.138 heavy chain variable region (DNA) |
| 42 | hAPRIL.138 light chain variable region (DNA) |
| 43 | hAPRIL.138 heavy chain variable region (AA) |
| 44 | hAPRIL.138 light chain variable region (AA) |
| 45 | hAPRIL.138 heavy chain CDR1 (AA) |
| 46 | hAPRIL.138 heavy chain CDR2 (AA) |
| 47 | hAPRIL.138 heavy chain CDR3 (AA) |
| 48 | hAPRIL.138 light chain CDR1 (AA) |
| 49 | hAPRIL.138 light chain CDR2 (AA) |
| 50 | hAPRIL.138 light chain CDR3 (AA) |

BRIEF DESCRIPTION OF THE FIGURES

FIG. 2A. Impact of APRIL quantification using a commercially available Biolegend ELISA assay by the presence of human serum. Two standard curves were generated using recombinant APRIL diluted in PBS+10% Foetal Calf Serum+20% human serum (HS) (referred to as PBS-FCS-HS) or diluted in PBS/1% BSA (referred to as PBS/BSA), at the concentrations of 100, 33.3, 11.1, 3.7, 1.23, 0.41, 0.136 and 0.04 ng/ml. FIG. 2B. Impact of APRIL quantification using commercially available BCMA-FC and APRILY-5 bio antibodies by the presence of human serum. Two standard curves were generated using recombinant APRIL diluted in PBS+10% Foetal Calf Serum+20% human serum (HS) (referred to as PBS-FCS-HS) or diluted in PBS/1% BSA (referred to as PBS/BSA), at the concentrations of 100, 33.3, 11.1, 3.7, 1.23, 0.41, 0.136 and 0.04 ng/ml. FIG. 2C. Impact of APRIL quantification using commercially available Sasha-2 and APRILY-5 antibodies by the presence of human serum. Two standard curves were generated using recombinant APRIL diluted in PBS+10% Foetal Calf Serum+20% human serum (HS) (referred to as PBS-FCS-HS) or diluted in PBS/1% BSA (referred to as PBS/BSA), at the concentrations of 100, 33.3, 11.1, 3.7, 1.23, 0.41, 0.136 and 0.04 ng/ml. FIG. 2D. Impact of APRIL quantification using commercially available R&D Systems ELISA by the presence of human serum. Two standard curves were generated using recombinant APRIL diluted in PBS+10% Foetal Calf Serum+20% human serum (HS) (referred to as PBS-FCS-HS) or diluted in PBS/1% BSA (referred to as PBS/BSA), at the concentrations of 100, 33.3, 11.1, 3.7, 1.23, 0.41, 0.136 and 0.04 ng/ml.

FIG. 4A. APRIL binding monoclonal antibodies were used to detect APRIL in the serum of CLL patients. Three independent patient's sera were used (CLL1, CLL3 and CLL6), which demonstrated varying amounts of APRIL. All APRIL binding antibodies display similar detection of APRIL in the three different patients independent of the amount of BCMA-Fc coated to capture APRIL (compare top with bottom for 500 ng/well versus 100 ng/well BCMA- Fc). FIG. 4B. Detection of APRIL in serum of CLL patients was determined for antibody hAPRIL.133 using ten more individual samples (CLL11-20) demonstrating varying amounts of APRIL.

DETAILED DESCRIPTION

Figure 1:
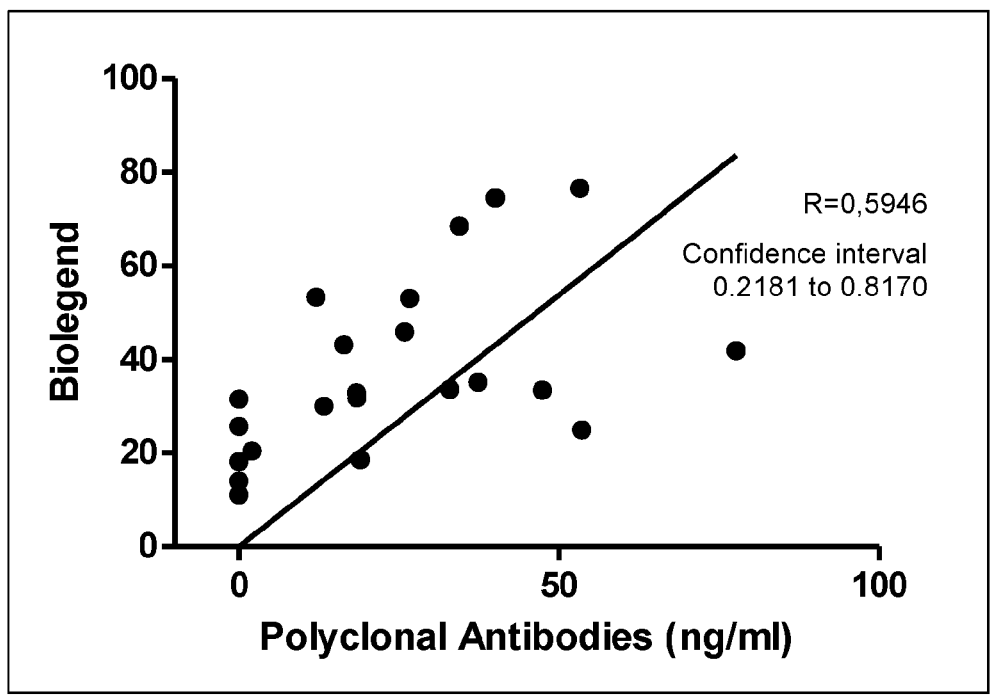
FIG. 1. Commercially available assay to detect APRIL (obtained from Biolegend) does not reproduce APRIL quantification in the presence of serum.
Human serum from colorectal cancer patients contain varying amounts of human APRIL as detected by the ELISA based on BCMA-Fc coating and polyclonal antibody for detection (x-axis, assay as described by Planelles et al., Haematologica. 2007 September; 92(9):1284-5) or as detected with the commercial Biolegend ELISA (y-axis). Comparison between both values per patient reveals limited correlation as depicted by the Spearman coefficient (R=0.5964).

In the method of the invention for obtaining APRIL-binding peptides a library of binder peptides is provided. The term "library" is known within the art and within the known meaning of this term a "library of binder peptides" may be understood to mean a collection or array of differing binder peptides. The term "binder peptides" or alternatively "binding peptides" within the context of a peptide library may be understood as referring to peptides having a potential capability of binding other compounds and/or structures, in particular epitopes, more in particular peptidic epitopes. Within the present invention binder peptides in particular have a potential APRIL-binding capability.

Antibodies (immunoglobulins) and binding fragments of antibodies, are known peptides having the potential capability to bind to other compounds and/or structures, including epitopes, such as peptidic epitopes. Thus within the present invention it is in particular envisaged to provide libraries of antibodies or antibody fragments. The skilled person will know how to obtain and thus how to provide a library of antibodies or antibody fragments.

Antibodies or antibody fragments may for example be isolated from antibody phage libraries generated using the techniques described in McCafferty et al., 1990, *Nature*, 348:552-554. Clackson et al., 1991, *Nature*, 352:624-628, and Marks et al., 1991, *J. Mol. Biol.* 222:581-597, who describe the isolation of murine and human antibodies, respectively, using phage libraries. Subsequent publications describe the production of high affinity (nM range) human antibodies by chain shuffling (Marks et al., 1992, *Bio/Technology*, 10:779-783), as well as combinatorial infection and in vivo recombination as a strategy for constructing very large phage libraries (Waterhouse et al., 1993, *Nuc. Acids Res.* 21:2265-2266).

Antibody or antibody fragments may be isolated from mRNA display libraries generated using techniques described in Fukuda et al., 2006, *Nuc. Acids Res.*, 34:e127, who describe the isolation of antibody fragments using mRNA display libraries.

Alternatively an antibody library may comprise a collection of lymphocytes, preferably splenocytes, collected from a mammal, such as a non-human mammal, immunized with an agent suitable for eliciting an APRIL-specific immune response in the mammal. Immunization of (non-human) mammals and collecting splenocytes (or other lymphocytes) is common practice within the field. The agent suitable for eliciting an APRIL-specific immune response used for immunization may be the APRIL protein or a part thereof, in particular in a purified form, most preferably in a substantially pure form. Alternatively immunization may be effected by DNA immunization using a nucleotide sequence, preferably a cDNA sequence, coding for APRIL or a part thereof. Methods and procedures for DNA immunization are known to the skilled person. Exemplary procedures for DNA immunization are presented in the examples.

Apart from a library of antibodies (or antibody fragments), a library of binding peptides engineered on non-immunoglobulin protein scaffolds may be provided. Examples of such protein scaffolds include, but are not limited to Adnectins, Affibodies, Anticalins and DARPins (Gebauer and Skerra, *Current opinion Chem. Biol.*, 2009, 13:245-255 and Caravella and Lugovskoy, *Current opinion Chem. Biol.*, 2010, 14:520-528). Selection methods for example include phage display to identify protein scaffolds that express APRIL-binding peptides.

In addition, combinatorial peptide libraries may be provided as the binder peptide library. For example, one-bead-one-compound combinatorial libraries are libraries that express a broad set of peptides on beads, where one bead is binding one peptide. After selection procedures, beads are recovered and the peptide is identified (Lam et al., *Methods*, 1996, 9:482-93; Xiao et al., *Comb. Chem. High Throughput Screen*, 2013, Mar. 13 (epub ahead of print) using for example mass-spectrometry methods.

In the method for obtaining APRIL-binding peptides, peptides binding specifically to APRIL are selected from the library of binder peptides by means of affinity selection. The affinity selection procedure uses a target peptide immobilized on a solid support. "Specifically" binds, when referring to a ligand/receptor, antibody/antigen, or other binding pair, indicates a binding process which is determinative of the presence of the protein, e.g., APRIL, in a heterogeneous population of proteins and/or other biologics. Thus, under designated conditions, a specified ligand/antigen binds to a particular receptor/antibody and does not bind in a significant amount to other proteins present in the sample.

The target peptide comprises a number of APRIL epitopes and an APRIL receptor-binding region of APRIL. The APRIL epitopes preferably are from a region outside the APRIL receptor-binding region of APRIL. As will be clear the number of APRIL epitopes and the APRIL receptor-binding region of APRIL can suitably be provided in the form of native APRIL or a derivative thereof. The use of native April as the target peptide is preferred.

Affinity selection procedures using an immobilized ligand for a binder peptide to be selected are known in the art. For example panning or biopanning procedures are known. As is known and as will be clear for the skilled person, a typical affinity selection procedure comprises three steps: capturing, washing and identification of captured binders.

For the affinity selection procedure employed in the method of the present invention, the capturing step involves binding of the binder peptides of the library with a target peptide comprising an APRIL receptor-binding region of APRIL. As is known in the art APRIL (at present) has two known natural receptors i.e. BCMA and TACI. Thus the term APRIL receptor may be understood as to mean BCMA or TACI. Although the invention to a large extend is exemplified with the use of BCMA as the APRIL receptor. The use of TACI is equally suitable. The region of APRIL involved in binding to its natural receptors is known (Hymowitz et al., 2005, *J. Biol. Chem.* 280: 7218-7227). The target peptide comprises this APRIL receptor-binding region of APRIL in a form that allows binding of an APRIL receptor (or a binding equivalent thereof). The target peptide is immobilized on a solid support to allow identification and/or isolation of binder peptides specifically interacting with the selected target. The term "immobilized" should be understood as meaning having a restricted, or reduce mobility. The restricted, or reduce mobility is relative to the washing medium, used in the washing step. The "immobilized" target peptide need not be directly bound to or interacting with the solid support. Instead it may have an interaction with a compound or moiety bound to or interacting with the solid support. Examples of means of immobilization of peptides include, but are not restricted to non-specific adherence to plastic, NH2-coupling to beads, binding to tosyl-activated beads or binding to Protein A beads. Methods for immobilization of peptides on solid supports are clear to the skilled person.

The target peptide in the affinity selection procedure employed in the method of the invention comprises an APRIL receptor-binding region of APRIL and a number of APRIL epitopes. The APRIL receptor-binding region of APRIL may be presented in the form of a complete APRIL protein or a part of an APRIL protein. The sequence of the APRIL protein or a part thereof preferably is of human origin. The APRIL epitopes may be present on the APRIL receptor-binding region of APRIL or on a different part of the target peptide. The selection of the APRIL receptor-binding region of APRIL and the APRIL epitopes is such that binding interaction of the target peptide with the shielding peptide is possible. In this description and the appended claims a number of should be understood as meaning one or more, such as 1, 2, 3, 4, 5, 6, 7 or more, every time when used, unless specifically stated differently.

In the method of the invention for obtaining APRIL-binding peptides the target peptide (comprising an APRIL-binding region of APRIL and a number of APRIL epitopes) is immobilized on the solid support in interaction with a shielding peptide comprising an APRIL binding region of an APRIL receptor or an APRIL binding equivalent thereof. The APRIL-binding region of the APRIL receptor may be presented in a complete APRIL receptor protein or in a part of an APRIL receptor protein. The sequence of the APRIL receptor protein or a part thereof preferably is of human origin.

As an alternative for the APRIL binding region of an APRIL receptor protein an APRIL binding region of an APRIL binding equivalent of such an APRIL receptor protein may be used. An APRIL binding equivalent of an APRIL receptor protein may for example be a peptide, such as an antibody, binding to APRIL at the APRIL-APRIL receptor interface. Such peptides may be selected from peptides interfering with the interaction of APRIL and a number of its receptors (BCMA or TACI). For example the hAPRIL.01A antibody disclosed in WO2010/100056 or an analogue thereof. Analogues of hAPRIL.01A are antibody analogues, in particular antibody fragments, as defined in this specification. Whether or not a certain APRIL-binding peptide, such as an APRIL-binding antibody, interferes with the interaction of APRIL and an APRIL receptor may be determined in accordance with the methodology described under "Receptor Blockade" in example 2 of WO2010/100056.

It should be noted that the target peptide may be immobilized on the solid support by its interaction with the shielding peptide, said shielding peptide being immobilized on the solid support by known means exemplified above.

The washing step follows the capturing step. In this step unbound elements (binder peptides and/or target peptides and/or shielding peptides and/or any other elements) are washed from the solid support by use of a washing medium, such as a washing liquid. By selecting the washing conditions the stringency of the selection may be selected. Such methods are clear to a skilled person. For example, washing procedures including cells will use Phosphate buffered saline or culture medium as a washing liquid. Washing liquid can include high salt (e.g. 1 M Sodium Chloride) or low salt (e.g. 50 mM Sodium Chloride) to influence the stringency (ionic strength) of washing procedures. Washing liquid can also include detergents, such as Nonidet P-40 to influence the stringency (hydrophobic strength) of washing procedures.

In the identification step following the washing step, binder peptides that remain in interaction with the target peptide after the washing step are identified. The identification step may comprise elution of binder peptides from the solid support where after the eluted binder peptides may be identified in any suitable way known. A skilled person can apply mass-spectrometry methods to identify peptides, RNA sequencing to identify RNA molecules encoding the binder peptide or DNA sequencing to identify cDNA molecules encoding the binder peptide. Alternatively identification may be done by using a labeling moiety, such as a fluorescent label, linked to either the binder peptides or the target peptide, such as is done in bio-microarray applications.

According to certain embodiments, the method of the invention may further comprise a step of negative selection of peptides binding to the solid support and/or the shielding peptide. In certain affinity selection procedures the use of such a negative selection step may result in APRIL-binding peptides having improved specificity for APRIL. The improvement being relative to APRIL-binding peptides obtained in methods not including the negative selection step.

In the negative selection step binder peptides are discarded if they have a higher affinity for the shielding peptide or the solid support than for the target peptide. The negative selection step may be performed prior or after the capturing step using the target peptide in interaction with the shielding peptide (the primary capturing step). According to certain embodiments the negative selection step is performed prior to the primary capturing step by including a negative capturing step involving binding of the binder peptides of the library to the shielding peptide (immobilized on the solid support) in the absence of the target peptide. In this negative pre-selection step unbound binder peptides are selected for use in the primary step. According to certain other embodiments the negative selection step is performed after the primary capturing step by including a negative capturing step involving binding, of the binder peptides selected in the primary capturing step, to the shielding peptide (immobilized on the solid support) in the absence of the target peptide. In this negative post-selection step unbound binder peptides are selected as the APRIL-binding peptides. For performing a negative selection step it is preferred that the immobilization of the target peptide is dependent on its interaction with the shielding peptide (the shielding peptide has a stronger interaction with the solid support than with the target peptide). In this embodiment target peptide may be brought in interaction with the shielding peptide immobilized on the solid support after the pre-selection test or the interaction of the target peptide and the immobilized shielding peptide may be disturbed for to the post-selection step.

In the procedure of the method of the invention described above, APRIL-binding peptides are identified and/or isolated. In order to facilitate production of the APRIL-binding peptides it may be beneficial to determine an amino acid sequence of a selected APRIL-binding peptide and/or a nucleotide sequence coding for the amino acid sequence of an APRIL-binding peptide identified and/or obtained with the method. This enables transfection of the nucleotide sequence coding for the APRIL-binding peptides to produce organisms capable of producing the APRIL-binding peptides with good efficiency. Depending on the library of binder peptides used, the nucleotide sequence coding for the APRIL-binding peptides may be determined and/or isolated with various methods available to the skilled person.

In case the library is a collection of lymphocytes collected from an immunized mammal the APRIL-binding peptide will be an immunoglobulin molecule presented on the cell-surface of a lymphocyte clone obtained. The nucleotide sequence coding for the APRIL-binding peptides may be obtained by isolating RNA from a culture of the lymphocyte clone, selectively amplifying the immunoglobulin sequence using immunoglobulin-specific primers followed by sequencing of the selectively amplified sequence.

In case the library is a collection of phages, the selected binding peptide will be an antibody or antibody fragment presented on the surface of the phage. The nucleotide encoding for the APRIL-binding peptide may be isolated by isolating DNA from the isolated phages followed by sequencing of the DNA.

In case the library is a collection of mRNAs displayed on a ribosome, the selected binding peptide will be displayed on a ribosome. The nucleotide encoding for the APRIL-binding peptide may be isolated by isolating the mRNA bound to the ribosome. The identity of the binding-peptide is determined by direct RNA sequencing or generation of cDNA complementary to the mRNA, followed by sequencing of the selectively amplified sequence.

In case the library is a collection of binding-peptides bound to beads (one-bead-one-compound library), one binding peptide is bound to one bead. The identity of the APRIL-binding peptide is determined by recovering the peptides from the beads selected in the affinity selection procedure, followed by mass-spectrometry procedures.

It will be clear that in the method of the invention for obtaining APRIL-binding peptides, reactions and processes such as the binding affinity selection process and associated processes such as capturing steps and washing steps may be performed in a suitable container, such as a reaction vessel, in particular vessels used on laboratory scale for such screening methods.

The invention further relates to an APRIL-binding peptide obtainable with the method according to the invention for obtaining APRIL-binding peptides. It will be clear to the skilled person that with the method of the invention a great number of different APRIL-binding peptides may be obtained. The binding peptides obtainable with the method of the invention share the common feature that, compared to known APRIL-binding peptides, they have a reduced interference with the binding of APRIL to its receptors. Thus they are able to better bind APRIL in complex with its receptors or binding equivalents thereof, such as hAPRIL.01A or analogues thereof. APRIL-binding peptides, such as antibodies, of the present invention will usually have a $K_D$ for their target (APRIL, preferably human APRIL) of about below $10^{-3}$ M, more usually below $10^{-6}$ M, typically below $10^{-7}$ M, more typically below $10^{-8}$ M, preferably below $10^{-9}$ M, and more preferably below $10^{-10}$ M, and most preferably below $10^{-11}$ M (see, e.g. Presta, et al., 2001, Thromb. Haemost. 85:379-389; Yang, et al., 2001, Crit. Rev. Oncol. Hematol. 38:17-23; Carnahan, et al., 2003, Clin. Cancer Res. (Suppl.) 9:3982s-3990s). According to certain embodiments the $K_D$ of the APRIL-binding peptides, such as antibodies, of the invention for their target (APRIL, preferably human APRIL) may be selected from $1 \cdot 10^{-6}$ to $0.5 \cdot 10^{-11}$ M, $1 \cdot 10^{-7}$ to $0.5 \cdot 10^{-11}$ M, $1 \cdot 10^{-8}$ to $0.5 \cdot 10^{-11}$ M, $1 \cdot 10^{-8}$ to $1 \cdot 10^{-11}$ M, preferably $5 \cdot 10^{-9}$ to $1 \cdot 10^{-11}$ M, more preferably $5 \cdot 10^{-9}$ to $1 \cdot 10^{-10}$ M. Binding affinities may be determined using standard analysis. According to certain embodiments the APRIL-binding peptides obtainable have an IC50 for inhibition of the APRIL receptor-APRIL interaction of at least $5 \cdot 10^{-9}$ M, preferably above $1 \cdot 10^{-8}$ M and more preferably above $1 \cdot 10^{-7}$ M and most preferably above $1 \cdot 10^{6}$ M. For example the IC50 for inhibition of the APRIL receptor-APRIL interaction may be from $5 \cdot 10^{-9}$ to $1 \cdot 10^{-4}$ M, such as $5 \cdot 10^{-9}$ to $1 \cdot 10^{-5}$ M, preferably $1 \cdot 10^{-8}$ to $1 \cdot 10^{-5}$ M, such as $1 \cdot 10^{-8}$ to $1 \cdot 10^{-6}$ M, $1 \cdot 10^{-8}$ to $1 \cdot 10^{-7}$ M, $1 \cdot 10^{-7}$ to $1 \cdot 10^{-5}$ M, or $1 \cdot 10^{-7}$ to $1 \cdot 10^{-6}$ M.

According to certain embodiments the obtainable APRIL-binding peptide is an immunoglobulin or a binding fragment of an immunoglobulin. In the present description and the appended claims the terms immunoglobulin and antibody are used as synonyms and are thus interchangeable. The term "antibody" refers to any form of antibody that exhibits a desired activity, in particular binding to a target. By binding to the target certain desired effects may be promoted. For example a compound or moiety associated, for example by being bound with the antibody, may be targeted to the target location. In the present invention the target is APRIL, preferably human APRIL. The antibody targeting APRIL can bind APRIL when APRIL is bound to its receptors or analogues thereof.

The term "antibody" is used in the broadest sense and specifically covers, but is not limited to, monoclonal antibodies (including full length monoclonal antibodies), polyclonal antibodies, and multispecific antibodies (e.g., bispecific antibodies). Within the present invention a peptide derived from a certain antibody may be considered an antibody analogue. The skilled person will understand that for a proper functioning of an antibody analogue within the context of this invention a derived antibody (or antibody analogue) will comprise antigen binding regions of its originating antibody. Antibody analogues in particular comprise antibody fragments, antibodies having modified effector function, chimeric antibodies and humanized antibodies as defined below.

"Antibody fragment" and "antibody binding fragment" mean antigen-binding fragments and comparable parts of an antibody, typically including at least a portion of the antigen binding or variable regions of the parental antibody. An antibody fragment retains at least some of the binding specificity of the parental antibody. For this an antibody fragment comprises a number of CDRs, in particular a number of CDRs of a $V_H$ region, such as CDR1, CDR2 and CDR3 of a $V_H$ region. In addition to the number of CDRs of a $V_H$ region, an antibody fragment may also comprise a number of CDRs of a $V_L$ region, such as CDR1, CDR2 and CDR3 of a $V_L$ region. According to certain embodiments antibody fragments may comprise CDR1, CDR2 and CDR3 of a $V_H$ region in conjunction with CDR1, CDR2 and CDR3 of a $V_L$ region. Typically, an antibody fragment retains at least 10% of the parental binding activity when that activity is expressed on a molar basis. Preferably, an antibody fragment retains at least 20%, 50%, 70%, 80%, 90%, 95% or 100% or more of the parental antibody's binding affinity for the target. Therefore, as is clear for the skilled person, "antibody fragments" in many applications may substitute antibodies and the term "antibody" should be understood as including "antibody fragments" when such a substitution is suitable. Examples of antibody fragments include, but are not limited to, Fab, Fab', F(ab')2, and Fv fragments; diabodies; linear antibodies; single-chain antibody molecules, e.g., sc-Fv, unibodies or duobodies (technology from Genmab); domain antibodies (technology from Domantis);

nanobodies (technology from Ablynx); and multispecific antibodies formed from antibody fragments. Engineered antibody variants are reviewed in Holliger and Hudson, 2005, Nat. Biotechnol. 23:1126-1136.

An "Fab fragment" is comprised of one light chain and the CH1 and variable regions of one heavy chain. The heavy chain of a Fab molecule cannot form a disulfide bond with another heavy chain molecule.

An "Fc" region contains two heavy chain fragments comprising the $C_H1$ and $C_H2$ domains of an antibody. The two heavy chain fragments are held together by two or more disulfide bonds and by hydrophobic interactions of the $C_H3$ domains.

An "Fab' fragment" contains one light chain and a portion of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a $F(ab')_2$ molecule.

An "$F(ab')_2$ fragment" contains two light chains and two heavy chains containing a portion of the constant region between the $C_H1$ and $C_H2$ domains, such that an interchain disulfide bond is formed between the two heavy chains. A $F(ab')_2$ fragment thus is composed of two Fab' fragments that are held together by a disulfide bond between the two heavy chains.

The "Fv region" comprises the variable regions from both the heavy and light chains, but lacks the constant regions.

A "single-chain Fv antibody" (or "scFv antibody") refers to antibody fragments comprising the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen binding. For a review of scFv, see Pluckthun, 1994, The Pharmacology of Monoclonal Antibodies, vol. 113, Rosenburg and Moore eds. Springer-Verlag, New York, pp. 269-315. See also, International Patent Application Publication No. WO 88/01649 and U.S. Pat. Nos. 4,946,778 and 5,260,203.

A "diabody" is a small antibody fragment with two antigen-binding sites. The fragments comprises a heavy chain variable domain ($V_H$) connected to a light chain variable domain ($V_L$) in the same polypeptide chain ($V_H$—$V_L$ or $V_L$—$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al., 1993, Proc. Natl. Acad. Sci. USA 90: 6444-6448.

A "domain antibody fragment" is an immunologically functional immunoglobulin fragment containing only the variable region of a heavy chain or the variable region of a light chain. In some instances, two or more $V_H$ regions are covalently joined with a peptide linker to create a bivalent domain antibody fragment. The two $V_H$ regions of a bivalent domain antibody fragment may target the same or different antigens.

An antibody fragment of the invention may comprise a sufficient portion of the constant region to permit dimerization (or multimerization) of heavy chains that have reduced disulfide linkage capability, for example where at least one of the hinge cysteines normally involved in inter-heavy chain disulfide linkage is altered with known methods available to the skilled person. In another embodiment, an antibody fragment, for example one that comprises the Fc region, retains at least one of the biological functions normally associated with the Fc region when present in an intact antibody, such as FcRn binding, antibody half life modulation, ADCC (antibody dependent cellular cytotoxicity) function, and/or complement binding (for example, where the antibody has a glycosylation profile necessary for ADCC function or complement binding).

In the present invention the antibody is directed against APRIL, preferably human APRIL, and thus comprises binding domains that bind to and/or interact with APRIL, preferably human APRIL. The antibody may be raised in an animal from a non-human species suitable for eliciting antibodies against human antigens. Alternatively, the antibody may be isolated from antibody phage libraries generated using the techniques described in McCafferty et al., 1990, Nature, 348:552-554. Clackson et al., 1991, Nature, 352:624-628, and Marks et al., 1991, J. Mol. Biol. 222:581-597. The skilled person will be able to select a suitable non-human species for eliciting antibodies against human antigens. For example a selection may be made from a non-human mammal, such as a rodent, including murine (rat or mouse) or hamster species, or alternatively a camelid species.

The antibody, when raised in a non-human species, preferably is chimerized with methods and techniques known in the art to form a "chimeric antibody".

The term "chimeric" antibody refers to antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (See, for example, U.S. Pat. No. 4,816,567 and Morrison et al., 1984, Proc. Natl. Acad. Sci. USA 81:6851-6855). Within the present invention a "chimeric antibody" preferably is a "humanized antibody".

As used herein, the term "humanized antibody" refers to forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The humanized forms of rodent antibodies will essentially comprise the same CDR sequences of the parental rodent antibodies, although certain amino acid substitutions may be included to increase affinity, increase stability of the humanized antibody, or for other reasons However, as CDR loop exchanges do not uniformly result in an antibody with the same binding properties as the antibody of origin, changes in framework residues (FR), residues involved in CDR loop support, might also be introduced in humanized antibodies to preserve antigen binding affinity (Kabat et al., 1991, J. Immunol. 147:1709).

The term "antibody" also includes "fully human" antibodies, i.e., antibodies that comprise human immunoglobulin protein sequences only. A fully human antibody may contain non-human, such as murine (rat or mouse) carbohydrate chains if produced in a mouse, in a non-human cell (e.g. mouse or hamster), or in a hybridoma derived from a murine cell. Similarly, "mouse antibody" or "rat antibody" refer to an antibody that comprises only mouse or rat immunoglobulin sequences, respectively. A fully human antibody may be generated in a human being, in a transgenic non-human animal having human immunoglobulin germline sequences, by phage display or other molecular biological methods. Also, recombinant immunoglobulins may also be made in transgenic mice. See Mendez et al., 1997, Nature Genetics 15:146-156. See also Abgenix, Medarex, MeMo and Kymab technologies.

The term "hypervariable region," as used herein, refers to the amino acid residues of an antibody which are responsible for antigen-binding. The hypervariable region comprises amino acid residues from a "complementarity determining region" or "CDR," defined by sequence alignment, for example residues 24-34 (L1), 50-56 (L2) and 89-97 (L3) in the light chain variable domain and 31-35 (H1), 50-65 (H2) and 95-102 (H3) in the heavy chain variable domain (see Kabat et al., 1991, Sequences of proteins of Immunological Interest, 5th Ed. Public Health Service, National Institutes of Health, Bethesda, Md.) and/or those residues from a "hypervariable loop" (HVL), as defined structurally, for example, residues 26-32 (L1), 50-52 (L2) and 91-96 (L3) in the light chain variable domain and 26-32 (H1), 53-55 (H2) and 96-101 (H3) in the heavy chain variable domain (see Chothia and Leskl, 1987, J. Mol. Biol. 196:901-917). "Framework" or "FR" residues are those variable domain residues other than the hypervariable region residues as herein defined.

According to certain embodiments an obtainable APRIL-binding peptide, such as an antibody, or an analogue thereof, comprises immunoglobulin $V_H$ domains, comprising CDR1, CDR2 and CDR3 sequences having at least 60%, such as at least 85%, preferably at least 90%, more preferably at least 95% sequence similarity with amino acid sequences selected from SEQ ID NO: 5, 6 and 7, or SEQ ID NO: 15, 16 and 17 or SEQ ID NO: 25, 26 and 27 or SEQ ID NO: 35, 36 and 37 or SEQ ID NO: 45, 46 and 47 such as a $V_H$ domain having at least 60%, such as at least 85%, preferably at least 90%, more preferably at least 95% sequence similarity with an amino acid sequence selected from SEQ ID NO.3, 13, 23, 33 or 43. As the skilled person will understand, the $V_H$ domain is primarily dominant in determining the binding affinity and specificity of antibodies. Thus effective binding may be obtained in the absence of the $V_L$ domain, such as in antibodies from camelids and camelised antibodies.

Said APRIL-binding peptide, such as an anti-APRIL antibody or analogue thereof, may comprise immunoglobulin $V_H$ and $V_L$ domains, comprising $V_H$ CDR1, $V_H$ CDR2 $V_H$ CDR3, $V_L$ CDR1, $V_L$ CDR2 and $V_L$ CDR3 sequences having at least 60%, such as at least 85%, preferably at least 90%, more preferably at least 95% sequence similarity with amino acid sequences selected from SEQ ID NO: 5, 6, 7, 8, 9 and 10 or SEQ ID NO: 15, 16, 17, 18, 19 and 20 or SEQ ID NO: 25, 26, 27, 28, 29 and 30 or SEQ ID NO: 35, 36, 37, 38, 39 and 40 or SEQ ID NO: 45, 46, 47, 48, 49 and 50 such as a $V_H$ and $V_L$ domain pair having at least 60%, such as at least 85%, preferably at least 90%, more preferably at least 95% sequence similarity with amino acid sequences selected from SEQ ID NO:3 and 4, or 13 and 14, or 23 and 24, or 33 and 34, or 43 and 44. DNA sequences coding for these various sequences can be determined by the skilled person on the basis of his knowledge of the genetic code. In table 2 below a number of DNA sequences coding for the $V_H$ and $V_L$ amino acid sequences is listed. The sequences are provided in the sequence listing.

As the skilled person will understand, "sequence similarity" refers to the extent to which individual nucleotide or peptide sequences are alike. The extent of similarity between two sequences is based on the extent of identity combined with the extent of conservative changes. The percentage of "sequence similarity" is the percentage of amino acids or nucleotides which is either identical or conservatively changed viz. "sequence similarity"=(% sequence identity)+(% conservative changes).

For the purpose of this invention "conservative changes" and "identity" are considered to be species of the broader term "similarity". Thus whenever, the term sequence "similarity" is used it embraces sequence "identity" and "conservative changes".

The term "sequence identity" is known to the skilled person. In order to determine the degree of sequence identity shared by two amino acid sequences or by two nucleic acid sequences, the sequences are aligned for optimal comparison purposes (e.g., gaps can be introduced in the sequence of a first amino acid or nucleic acid sequence for optimal alignment with a second amino or nucleic acid sequence). Such alignment may be carried out over the full lengths of the sequences being compared. Alternatively, the alignment may be carried out over a shorter comparison length, for example over about 20, about 50, about 100 or more nucleic acids/bases or amino acids.

The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The degree of identity shared between sequences is typically expressed in terms of percentage identity between the two sequences and is a function of the number of identical positions shared by identical residues in the sequences (i.e., % identity=number of identical residues at corresponding positions/total number of positions×100). Preferably, the two sequences being compared are of the same or substantially the same length.

The percentage of "conservative changes" may be determined similar to the percentage of sequence identity. However, in this case changes at a specific location of an amino acid or nucleotide sequence that are likely to preserve the functional properties of the original residue are scored as if no change occurred.

For amino acid sequences the relevant functional properties are the physico-chemical properties of the amino acids. A conservative substitution for an amino acid in a polypeptide of the invention may be selected from other members of the class to which the amino acid belongs. For example, it is well-known in the art of protein biochemistry that an amino acid belonging to a grouping of amino acids having a particular size or characteristic (such as charge, hydrophobicity and hydrophilicity) can be substituted for another amino acid without substantially altering the activity of a protein, particularly in regions of the protein that are not directly associated with biological activity (see, e.g., Watson, et al., *Molecular Biology of the Gene*, The Benjamin/Cummings Pub. Co., p. 224 (4th Edition 1987)). For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Conservative substitutions include, for example, Lys for Arg and vice versa to maintain a positive charge; Glu for Asp and vice versa to maintain a negative charge; Ser for Thr and vice versa so that a free —OH is maintained; and Gln for Asn and vice versa to maintain a free —NH$_2$.

Exemplary conservative substitutions in the amino acid sequence of the APRIL binding peptides of the invention can be made in accordance with those set forth below as follows:
Exemplary Conservative Amino Acid Substitutions

| Original residue | Conservative substitution |
|---|---|
| Ala (A) | Gly; Ser |
| Arg (R) | Lys, His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

For nucleotide sequences the relevant functional properties is mainly the biological information that a certain nucleotide carries within the open reading frame of the sequence in relation to the transcription and/or translation machinery. It is common knowledge that the genetic code has degeneracy (or redundancy) and that multiple codons may carry the same information in respect of the amino acid for which they code. For example in certain species the amino acid leucine is coded by UUA, UUG, CUU, CUC, CUA, CUG codons (or IT TTG, CTT, CTC, CTA, CTG for DNA), and the amino acid serine is specified by UCA, UCG, UCC, UCU, AGU, AGC (or TCA, TCG, TCC, TCT, AGT, AGC for DNA). Nucleotide changes that do not alter the translated information are considered conservative changes.

The skilled person will be aware of the fact that several different computer programs, using different mathematical algorithms, are available to determine the identity between two sequences. For instance, use can be made of a computer program employing the Needleman and Wunsch algorithm (Needleman et al. (1970)). According to an embodiment the computer program is the GAP program in the Accelerys GCG software package (Accelerys Inc., San Diego U.S. A). Substitution matrices that may be used are for example a BLOSUM 62 matrix or a PAM250 matrix, with a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms.

According to an embodiment the percent identity between two nucleotide sequences is determined using the GAP program in the Accelrys GCG software package (Accelerys Inc., San Diego U.S. A) A NWSgapdna CMP matrix and a gap weight of 40, 50, 60, 70, or 80 and a length weight of 1, 2, 3, 4, 5, or 6 is used.

In another embodiment, the percent identity of two amino acid or nucleotide sequences is determined using the algorithm of E. Meyers and W. Miller (Meyers et al. (1989)) which has been incorporated into the ALIGN program (version 2.0) (available at the ALIGN Query using sequence data of the Genestream server IGH Montpellier France http://vegajgh.mrs.fr/bin align-guess.cgi) using a PAM120 weight residue table, a gap length penalty of 12 and a gap penalty of 4.

For the present invention it is most preferred to use BLAST (Basic Local Alignment Tool) to determine the percentage identity and/or similarity between nucleotide or amino acid sequences.

Queries using the BLASTn, BLASTp, BLASTx, tBLASTn and tBLASTx programs of Altschul et al. (1990) may be posted via the online versions of BLAST accessible via http://www. ncbi.nlm.nih.gov.Alternatively a standalone version of BLAST {e.g., version 2.2.24 (released 23 Aug. 2010)) downloadable also via the NCBI internet site may be used. Preferably BLAST queries are performed with the following parameters. To determine the percentage identity and/or similarity between amino acid sequences: algorithm: blastp; word size: 3; scoring matrix: BLOSUM62; gap costs: Existence: 11, Extension: 1; compositional adjustments: conditional compositional score matrix adjustment; filter: off; mask: off. To determine the percentage identity and/or similarity between nucleotide sequences: algorithm: blastn; word size: 11; max matches in query range: 0; match/mismatch scores: 2, –3; gap costs: Existence: 5, Extension: 2; filter: low complexity regions; mask: mask for lookup table only.

The percentage of "conservative changes" may be determined similar to the percentage of sequence identity with the aid of the indicated algorithms and computer programs. Some computer programs, e.g., BLASTp, present the number/percentage of positives (=similarity) and the number/percentage of identity. The percentage of conservative changes may be derived therefrom by subtracting the percentage of identity from the percentage of positives/similarity (percentage conservative changes=percentage similarity–percentage identity).

On the basis of the sequence information available for the APRIL-binding peptide, further manipulations are possible. If the APRIL-binding peptide is an antibody, the antibody DNA also may be modified, for example, by substituting the coding sequence for human heavy- and light-chain constant domains in place of the homologous murine sequences (U.S. Pat. No. 4,816,567; Morrison, et al., 1984, *Proc. Natl Acad. Sci. USA,* 81:6851), or by covalently joining to the immunoglobulin coding sequence all or part of the coding sequence for non-immunoglobulin material (e.g., protein domains). Typically such non-immunoglobulin material is substituted for the constant domains of an antibody, or is substituted for the variable domains of one antigen-combining site of an antibody to create a chimeric bivalent antibody comprising one antigen-combining site having specificity for an antigen and another antigen-combining site having specificity for a different antigen.

A camelized antibody is heavy chain only antibody that is derived from a mouse antibody. Camelization can be performed following the method of Tanha et al., *Protein Eng Des Sel.,* 2006, 19:503-9.

A humanized antibody has one or more amino acid residues from a source that is non-human. The non-human amino acid residues are often referred to as "import" residues, and are typically taken from an "import" variable domain. Humanization can be performed generally following the method of Winter and co-workers (Jones et al., 1986, Nature 321:522-525; Riechmann et al., 1988, Nature, 332: 323-327; Verhoeyen et al., 1988, Science 239:1534-1536), by substituting rodent CDRs or CDR sequences for the corresponding sequences of a human antibody. Accordingly, such "humanized" antibodies are antibodies wherein substantially less than an intact human variable domain has been substituted by the corresponding sequence from a non-human species. In practice, humanized antibodies are typically human antibodies in which some CDR residues and possibly some FR residues are substituted by residues from analogous sites in non-human, for example, rodent antibodies.

The choice of human variable domains, both light and heavy, to be used in making the humanized antibodies is very important if a reduce antigenicity is relevant. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., 1987, J. Immunol. 151:2296; Chothia et al., 1987, J. Mol. Biol. 196:901). Another method uses a particular framework derived from the consensus sequence of all human antibodies of a particular subgroup of light or heavy chains. The same framework may be used for several different humanized antibodies (Carter et al., 1992, Proc. Natl. Acad. Sci. USA 89:4285; Presta et al., 1993, J. Immnol. 151:2623).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Humanization of antibodies is a straightforward protein engineering task. Nearly all murine antibodies can be humanized by CDR grafting, resulting in the retention of antigen binding. See, Lo, Benny, K. C., editor, in Antibody Engineering: Methods and Protocols, volume 248, Humana Press, New Jersey, 2004.

Amino acid sequence variants of humanized anti-APRIL antibodies are prepared by introducing appropriate nucleotide changes into the humanized anti-APRIL antibodies' DNAs, or by peptide synthesis. Such variants include, for example, deletions from, and/or insertions into, and/or substitutions of, residues within the amino acid sequences shown for the humanized anti-APRIL antibodies. Any combination of deletion, insertion, and substitution is made to arrive at the final construct, provided that the final construct possesses the desired characteristics. The amino acid changes also may alter post-translational processes of the humanized anti-APRIL antibodies, such as changing the number or position of glycosylation sites.

A useful method for identification of certain residues or regions of the humanized anti-APRIL antibodies polypeptides that are preferred locations for mutagenesis is called "alanine scanning mutagenesis," as described by Cunningham and Wells, 1989, Science 244: 1081-1085. Here, a residue or group of target residues are identified (e.g., charged residues such as Arg, Asp, His, Lys, and Glu) and replaced by a neutral or negatively charged amino acid (most preferably alanine or polyalanine) to affect the interaction of the amino acids with APRIL antigen. The amino acid residues demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, Ala scanning or random mutagenesis is conducted at the target codon or region and the expressed humanized anti-APRIL antibodies' variants are screened for the desired activity.

Ordinarily, amino acid sequence variants of the humanized anti-APRIL antibodies will have an amino acid sequence having at least 75% amino acid sequence identity with the original mouse antibody amino acid sequences of either the heavy or the light chain more preferably at least 80%, more preferably at least 85%, more preferably at least 90%, and most preferably at least 95%, 98% or 99%. Identity or homology with respect to this sequence is defined herein as the percentage of amino acid residues in the candidate sequence that are identical with the humanized residues, after aligning the sequences and introducing gaps, if necessary, to achieve the maximum percent sequence identity, and not considering any conservative substitutions as part of the sequence identity. None of N-terminal, C-terminal, or internal extensions, deletions, or insertions into the antibody sequence shall be construed as affecting sequence identity or homology. The percentage of identity between two sequences can be determined with computer application such as SeqMan II (DNAstar Inc, version 5.05). Using this program two sequences can be aligned using the optimal alignment algorithm of Smith and Waterman (1981) (Journal of Molecular Biology 147: 195-197). After alignment of the two sequences the percentage identity can be calculated by dividing the number of identical amino acids between the two sequences by the length of the aligned sequences minus the length of all gaps.

Antibodies having the characteristics identified herein as being desirable in humanized anti-APRIL antibodies can be screened for inhibitory biologic activity in vitro or suitable binding affinity. To screen for antibodies that bind to the epitope on human APRIL, a routine cross-blocking assay such as that described in Antibodies, A Laboratory Manual, Cold Spring Harbor Laboratory, Ed Harlow and David Lane (1988), can be performed. Antibodies that bind to the same epitope are likely to cross-block in such assays, but not all cross-blocking antibodies will necessarily bind at precisely the same epitope since cross-blocking may result from steric hindrance of antibody binding by antibodies bind at overlapping epitopes, or even nearby non-overlapping epitopes.

Alternatively, epitope mapping, e.g., as described in Champe et al., 1995, J. Biol. Chem. 270:1388-1394, can be performed to determine whether the antibody binds an epitope of interest. "Alanine scanning mutagenesis," as described by Cunningham and Wells, 1989, Science 244: 1081-1085, or some other form of point mutagenesis of amino acid residues in human APRIL may also be used to determine the functional epitope for anti-APRIL antibodies of the present invention. Another method to map the epitope of an antibody is to study binding of the antibody to synthetic linear and CLIPS peptides that can be screened using credit-card format mini PEPSCAN cards as described by Medema et al. (WO/2010/100056), Slootstra et al. (Slootstra et al., 1996, Mol. Diversity 1: 87-96) and Timmerman et al. (Timmerman et al., 2007, J. Mol. Recognit. 20: 283-299). The binding of antibodies to each peptide is determined in a PEPSCAN-based enzyme-linked immuno assay (ELISA).

Additional antibodies binding to the same epitope as an antibody of the present invention may be obtained, for example, by screening of antibodies raised against APRIL for binding to the epitope, or by immunization of an animal with a peptide comprising a fragment of human APRIL comprising the epitope sequences. Antibodies that bind to the same functional epitope might be expected to exhibit similar biological activities, such as blocking receptor binding, and such activities can be confirmed by functional assays of the antibodies.

Other APRIL-binding peptides to the same epitope as an antibody of the present invention may be obtained, for example, by preselecting binding peptides using the selection technology of the invention and a library displaying binding peptides. Binding peptides that bind to the same functional epitope might be expected to exhibit similar biological activities, such as blocking receptor binding, and such activities can be confirmed by functional assays of the antibodies.

Affinities of APRIL-binding peptides for APRIL may be determined using standard analysis. Preferred binding peptides such as e.g. antibodies are those that bind human APRIL with a Kd value of below about $1\times10^{-7}$; preferably below about $1\times10^{-8}$; more preferably below about $1\times10^{-9}$; and most preferably below about $1\times10^{-10}$ or even below $1\times10^{-11}$ M.

As used herein, the term "about" refers to a value that is within an acceptable error range for the particular value as determined by one of ordinary skill in the art, which will depend in part on how the value is measured or determined, i.e. the limitations of the measurement system. For example, "about" can mean within 1 or more than 1 standard deviation per the practice in the art. Alternatively, "about" or "comprising essentially of" can mean a range of up to 20%. Furthermore, particularly with respect to biological systems or processes, the terms can mean up to an order of magnitude or up to 5-fold of a value. When particular values are provided in the application and claims, unless otherwise stated, the meaning of "about" or "comprising essentially of" should be assumed to be within an acceptable error range for that particular value.

An antibody can be selected from any class of immunoglobulins, including IgM, IgG, IgD, IgA, and IgE. Preferably, the antibody is an IgG antibody. Any isotype of IgG can be used, including IgG1, IgG2, IgG3, and IgG4. Variants of the IgG isotypes are also contemplated. An humanized antibody may comprise sequences from more than one class or isotype. Optimization of the necessary constant domain sequences to generate the desired biologic activity is readily achieved by screening the antibodies in the biological assays described in the Examples.

Likewise, either class of light chain can be used in the compositions and methods herein. Specifically, kappa, lambda, or variants thereof are useful in the present compositions and methods.

The APRIL-binding peptide, such as anti-APRIL antibody or antibody analogue thereof, of the invention may be conjugated with a label, such as a label selected from fluorescent or chemilluminescent labels, including fluorophores such as rare earth chelates, fluorescein and its derivatives, rhodamine and its derivatives, isothiocyanate, phycoerythrin, phycocyanin, allophycocyanin, o-phthaladehyde, fluorescamine, $^{152}$Eu, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels and stable free radicals.

Any suitable method known in the art for conjugating protein molecules to the various moieties may be employed, including those methods described by Hunter et al., 1962, Nature 144:945; David et al., 1974, Biochemistry 13:1014; Pain et al., 1981, J. Immunol. Meth. 40:219; and Nygren, J., 1982, Histochem. and Cytochem. 30:407. Methods for conjugating antibodies and proteins are conventional and well known in the art.

According to certain embodiments the APRIL-binding peptide obtainable with the method of the invention is a binding peptide obtainable from a combinatorial peptide library. Such a APRIL-binding peptide need not be based on an antibody structure and thus may be a non-antibody binding peptide. Examples include APRIL-binding peptide derived from one-bead-one-peptide libraries. Other examples include APRIL-binding peptides based on engineered protein scaffolds, such as Adnectins, Affibodies, Anticalins and DARPins.

A further aspect of the invention relates to a cell comprising a nucleotide sequence coding for an APRIL-binding peptide obtainable with the method of the invention for obtaining APRIL-binding peptides. As discussed above the nucleotide sequence coding for an APRIL-binding peptide can be determined and/or isolated with different procedures, depending on the library of binder peptides used. Thus nucleotide sequences coding for a APRIL-binding peptide of the invention may be obtained. Such nucleotide sequences may be used for transfection of a host-cell. The cell thus may be a genetically modified cell. In particular the cell may be genetically modified by comprising the nucleotide coding for the APRIL-binding peptide as a heterologous nucleotide sequence.

The host cell may be a cloning host or an expression host. When selected as an expression host, the host cell expression system preferably is capable of and more preferably optimized for production of heterologous peptides, such as antibodies or antibody fragments. The host-cell may be from a unicellular organism or from a multicellular organism and may be selected from E. coli cells, simian COS cells, Chinese hamster ovary (CHO) cells, or myeloma cells that do not otherwise produce immunoglobulin protein or APRIL-binding peptide. For transfection, isolated DNA may be inserted into expression vectors, which are then transfected into host cells.

Alternatively, it is also possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., 1993, *Proc. Natl. Acad. Sci. USA* 90:2551; Jakobovits et al., 1993, *Nature* 362:255-258; Bruggermann et al., 1993, *Year in Immunology* 7:33; and Duchosal et al., 1992, *Nature* 355:258.

With the use of the cell according to the invention the APRIL-binding peptide may be produced. Thus a further aspect of the invention relates to a process for producing a APRIL-binding peptide comprising providing cells according to the invention, culturing said cells and allowing the cells to express and preferably secrete the APRIL-binding peptide.

The APRIL binding peptide may be isolated from the host cell expression system and various procedures for this are readily available to the skilled person. The specific procedure best suited will depend on the host cell expression system used and the skilled person will be able to make suitable selections on the basis of the common general knowledge available.

When using recombinant techniques, the APRIL-binding peptide, for example an antibody (or analogue) can be produced intracellularly, in the periplasmic space, or directly secreted into the medium. If the APRIL-binding peptide is produced intracellularly, as a first step, the particulate debris, either host cells or lysed fragments, is removed, for example, by centrifugation or ultrafiltration. Carter et al., 1992, *Bio/Technology* 10:163-167 describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the APRIL-binding peptide is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The APRIL-binding peptide composition prepared from the cells can be purified using, for example, hydroxylapatite chromatography, gel electrophoresis, dialysis, and affinity chromatography, with affinity chromatography being a particularly advantageous purification technique. The suitability of protein A as an affinity ligand for immoglobulins depends on the species and isotype of any immunoglobulin Fc region that is present in its protein sequence. Protein A can be used to purify antibodies that are based on human Ig.gamma1, Ig.gamma2, or Ig.gamma4 heavy chains (Lindmark et al., 1983, *J. Immunol. Meth.* 62:1-13). Protein G is recommended for all mouse isotypes and for human .gamma.3 (Guss et al., 1986, *EMBO J* 5:1567-1575). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the APRIL-binding peptide is an antibody and comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

The APRIL-binding peptide, for example an immunoglobulin, including a binding fragment of an immunoglobulin, obtainable with the process for production of an APRIL-binding peptide is a further aspect of the invention. This APRIL-binding peptide in general will have a peptide sequence within the definition of the APRIL-binding peptide obtainable with the method for obtaining an APRIL-binding peptide. However, differences may be present in respect of post-translation modifications such as glycosylation profiles. For example, antibodies lacking the core fucose residues has been shown to display enhanced ADCC activity. Modulation of glycosylation of patterns of antibodies is know to a skilled person. For example, the GlycoFi technology allows specific modulation of glycosylation of antibodies to display the desired level of Fc-effector function (Beck et al., *Expert Opin Drug Discov.*, 2010, 5:95-111.)

The APRIL-binding peptide, obtainable with the process for production of an APRIL-binding peptide may be an isolated antibody. An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In some embodiments, the peptide will be purified (1) to represent at least 50%, such as at least 60%, preferably at least 80%, such as, at least 90% by weight of protein in the composition containing the peptide, for example as determined by the Lowry method, and most preferably more than 95%, such as at least 99% by weight of protein in the composition containing the peptide, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., 1975, *Nature* 256:495, or may be made by recombinant DNA methods (see, for example, U.S. Pat. No. 4,816,567). The "monoclonal antibodies" may also be isolated from phage antibody libraries using the techniques described in Clackson et al., 1991, *Nature* 352:624-628 and Marks et al., 1991, J. Mol. Biol. 222:581-597, for example. The monoclonal antibodies herein specifically include "chimeric" antibodies.

Monoclonal antibodies can be made according to knowledge and skill in the art of injecting test subjects with human APRIL antigen and then generating hybridomas expressing antibodies having the desired sequence or functional characteristics. DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA.

The APRIL-binding peptide obtainable with the process of the invention for producing a APRIL-binding peptide, such as an antibody, or an analogue thereof, may comprise immunoglobulin $V_H$ domains, comprising CDR1, CDR2 and CDR3 sequences having at least 60%, such as at least 85%, preferably at least 90%, more preferably at least 95% sequence similarity with amino acid sequences respectively selected from SEQ ID NO: 5, 6 and 7, or SEQ ID NO: 15, 16 and 17 or SEQ ID NO: 25, 26 and 27 or SEQ ID NO: 35, 36 and 37 or SEQ ID NO: 45, 46 and 47 such as a $V_H$ domain having at least 60%, such as at least 85%, preferably at least 90%, more preferably at least 95% sequence similarity with an amino acid sequence selected from SEQ ID NO.3, 13, 23, 33 or 43.

Said APRIL binding peptide, such as an anti-APRIL antibody or analogue thereof, may comprise immunoglobulin $V_H$ and $V_L$ domains, comprising $V_H$ CDR1, $V_H$ CDR2 $V_H$ CDR3, $V_L$ CDR1, $V_L$ CDR2 and $V_L$ CDR3 sequences having at least 60%, such as at least 85%, preferably at least 90%, more preferably at least 95% sequence similarity with amino acid sequences respectively selected from SEQ ID NO: 5, 6, 7, 8, 9 and 10 or SEQ ID NO: 15, 16, 17, 18, 19 and 20 or SEQ ID NO: 25, 26, 27, 28, 29 and 30 or SEQ ID NO: 35, 36, 37, 38, 39 and 40 or SEQ ID NO: 45, 46, 47, 48, 49 and 50 such as a $V_H$ and $V_L$ domain pair having at least 60%, such as at least 85%, preferably at least 90%, more preferably at least 95% sequence similarity with amino acid sequences respectively selected from SEQ ID NO:3 and 4, or 13 and 14, or 23 and 24, or 33 and 34, or 43 and 44. DNA sequences coding for these various sequences can be determined by the skilled person on the basis of his knowledge of the genetic code. In table 2 below a number of DNA sequences coding for the $V_H$ and $V_L$ amino acid sequences is listed. The sequences are provided in the sequence listing.

The APRIL-binding peptide according to the invention finds use as a diagnostic tool and/or an analytical tool, preferably for ex vivo diagnostic methods. Thus further aspects of the invention relate to such uses of the APRIL-binding peptide. For example the APRIL-binding peptide may be used for detecting APRIL in a sample from a subject, such as a tissue sample, whole blood or a blood-derived sample, such as plasma or serum. Alternatively, the APRIL-binding peptide may be used for detecting APRIL on specific cells, such as cells derived from tissue, blood or a culture. Such a test may be aimed at diagnosing a condition associated with altered APRIL levels, such as a condition selected from cancers, conditions associated with inflammation, sepsis, allergies, autoimmune diseases or infections, such as bacteremia. The test may be used in the diagnosis for determining whether or not a subject suffers from a condition associated with altered APRIL levels. In this case in general it will be evaluated whether or not a subject has an elevated (above normal) APRIL level. The present norm for normal human serum APRIL levels is about 1-10 ng/ml (Planelles et al., 2007, Haematologica 92, 1284-5). Thus within the present invention an altered APRIL level may be an elevated APRIL level, such as an APRIL level above 10 ng/ml such as above 15, 30, 50 or 100 ng/ml. Or, in case the normal APRIL level of a particular subject is known (e.g. from a number of determinations done at a number of specific times considered as associated with normal APRIL levels), an elevated APRIL level may be determined relative to the normal level as determined for the subject. Alternatively the test may be used to evaluate the outcome of a treatment that a subject receives to cure and/or stabilize the condition associated with altered APRIL levels, from which the subject suffers. In this case in general it will be evaluated whether or not elevated APRIL levels in a subject decrease to closer to what is considered normal. It will be evident that after a subject has been positively diagnosed to suffer from a condition associated with altered APRIL levels, in particular elevated APRIL levels, diagnosis may continue to evaluate the outcome of a treatment that said subject receives to cure and/or stabilize the condition associated with altered APRIL levels.

A cancer for which tests employing an APRIL-binding peptide of the invention may be useful may be selected from leukemia, acute lymphocytic leukemia, acute myelocytic leukemia, myeloblasts promyelocyte, myelomonocytic monocytic erythroleukemia, chronic leukemia, chronic myelocytic (granulocytic) leukemia, chronic lymphocytic leukemia, mantle cell lymphoma, primary central nervous system lymphoma, Burkitt's lymphoma and marginal zone B cell lymphoma, Polycythemia vera Lymphoma, Hodgkin's disease, non-Hodgkin's disease, multiple myeloma, Waldenstrom's macroglobulinemia, heavy chain disease, solid tumors, sarcomas, and carcinomas, fibrosarcoma, myxosarcoma, liposarcoma, chrondrosarcoma, osteogenic sarcoma, osteosarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon sarcoma, colorectal carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, retinoblastoma, nasopharyngeal carcinoma, esophageal carcinoma, basal cell carcinoma, biliary tract cancer, bladder cancer, bone cancer, brain and central nervous system (CNS) cancer, cervical cancer, choriocarcinoma, colorectal cancers, connective tissue cancer, cancer of the digestive system, endometrial cancer, esophageal cancer, eye cancer, head and neck cancer, gastric cancer, intraepithelial neoplasm, kidney cancer, larynx cancer, liver cancer, lung cancer (small cell, large cell), melanoma, neuroblastoma; oral cavity cancer (for example lip, tongue, mouth and pharynx), ovarian cancer, pancreatic cancer, retinoblastoma, rhabdomyosarcoma, rectal cancer; cancer of the respiratory system, sarcoma, skin cancer, stomach cancer, testicular cancer, thyroid cancer, uterine cancer, and cancer of the urinary system.

Conditions associated with inflammation for which tests employing an APRIL-binding peptide of the invention may be useful are atherosclerosis, acne vulgaris, celiac disease, chronic prostatitis, glomerulonephritis, hypersensitivities, reperfusion injury, sarcoidosis, transplant rejection, vasculitis, interstitial cystitis, and conditions associated with sterile inflammation including Muckle-Wells syndrome and other autoinflammatory disorders.

Another condition for which tests employing an APRIL-binding peptide of the invention may be useful is sepsis and/or associated conditions, such as systemic inflammatory response syndrome (SIRS). The pathology of sepsis is known to the skilled person. In particular the skilled person will understand that sepsis may be defined as an infection-induced syndrome involving two or more of the following features of systemic inflammation: fever or hypothermia, leukocytosis or leukopenia, tachycardia, and tachypnea or a supranormal minute ventilation. The skilled person will also know that the development of sepsis in a subject may follow a course, progressing from systemic inflammatory response syndrome ("SIRS")-negative, to SIRS-positive, and then to sepsis, which may then progress to severe sepsis, septic shock, multiple organ dysfunction ("MOD"), and ultimately death. Sepsis may also arise in an infected subject when the subject subsequently develops SIRS. As such "Sepsis" may be defined as the systemic host response to infection with SIRS plus a documented infection. "Severe sepsis" is associated with MOD, hypotension, disseminated intravascular coagulation ("DIC") or hypoperfusion abnormalities, including lactic acidosis, oliguria, and changes in mental status. "Septic shock" is commonly defined as sepsis-induced hypotension that is resistant to fluid resuscitation with the additional presence of hypoperfusion abnormalities.

An autoimmune disease for which tests employing an APRIL-binding peptide of the invention may be useful may be selected from multiple sclerosis, rheumatoid arthritis, type 1 diabetes, psoriasis, Crohn's disease and other inflammatory bowel diseases such as ulcerative colitis, systemic lupus erythematosus (SLE), autoimmune encephalomyelitis, myasthenia gravis (MG), Hashimoto's thyroiditis, Goodpasture's syndrome, pemphigus, Graves disease, autoimmune hemolytic anemia, autoimmune thrombocytopenic purpura, scleroderma with anti-collagen antibodies, mixed connective tissue disease, polypyositis, pernicious anemia, idiopathic Addison's disease, autoimmune associated infertility, glomerulonephritis, crescentic glomerulonephritis, proliferative glomerulonephritis, bullous pemphigoid, Sjogren's syndrome, psoriatic arthritis, insulin resistance, autoimmune diabetes mellitus, autoimmune hepatitis, autoimmune hemophilia, autoimmune lymphoproliferative syndrome (ALPS), autoimmune hepatitis, autoimmune hemophilia, autoimmune lymphoproliferative syndrome, autoimmune uveoretinitis, Guillain-Bare syndrome, arteriosclerosis and Alzheimer's disease.

Exemplary allergic disorders, for which tests employing an APRIL-binding peptide of the invention may include, but are not limited to allergic conjunctivitis, vernal conjunctivitis, vernal keratoconjunctivitis, and giant papillary conjunctivitis; nasal allergic disorders, including allergic rhinitis and sinusitis; otic allergic disorders, including eustachian tube itching; allergic disorders of the upper and lower airways, including intrinsic and extrinsic asthma; allergic disorders of the skin, including dermatitis, eczema and urticaria; and allergic disorders of the gastrointestinal tract.

Some examples of pathogenic viruses causing infections include HIV, hepatitis (A, B, C, D or E), herpes virus (e.g., VZV, HSV-1, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections include *chlamydia*, rickettsial bacteria, mycobacteria, staphylococci, streptococci, pneumonococci, meningococci and conococci, *klebsiella, proteus, serratia, pseudomonas, legionella*, diphtheria, *salmonella*, bacilli, cholera, tetanus, botulism, anthrax, plague, leptospirosis, and Lyme disease bacteria.

Some examples of pathogenic fungi causing infections, include *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizophus*), *Sporothrix schenkii, Blastomyces dermatitidis, Paracoccidioides brasiliensis, Coccidioides immitis* and *Histoplasma capsulatum*.

Some examples of pathogenic parasites causing infections include *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*.

For diagnostic applications, the APRIL-binding peptide of the invention typically will be linked (either directly or indirectly) to a detectable labeling group, the signaling moiety. Numerous labeling moieties are available which can be generally grouped into the following categories: biotin, fluorochromes, radionucleotides, enzymes, iodine, and biosynthetic labels. Also, in case the APRIL-binding peptide is an antibody, or an analogue thereof, the Fc-chain may serve as a labeling moiety. Furthermore Fc-chains may be added to non-antibody binding peptides to serve as labels. There are numerous antibodies on the market targeting Fc-chains from various species such as anti-mouse and anti-human antibodies. These are available with various labels and may be used with known methods to target the Fc-chain of an anti-APRIL antibody of the invention. Thus, in case an anti-APRIL antibody is used, it is preferred that it is antigenically distict from other proteins present in the test (e.g. by comprising at least predominantly protein sequences from a xenogenic source), such as APRIL and the APRIL receptor (or the binding equivalent thereof). This facilitates targeting of the Fc-chain of the anti-APRIL antibody with labeled antibodies in the detection process. The skilled person will know that for chimeric antibodies, the Fc-chain will predominantly determine the antigenicity of an antibody.

According to certain embodiments of test methods, the APRIL-binding peptide is detected in a sample from a subject and the presence of the APRIL-binding peptide is used as an indicator for the presence of APRIL. In these embodiments the APRIL-binding peptide in general will be used in a soluble form. According to certain other embodiments of test methods, the APRIL-binding peptide is immobilized on a solid support and is used as a capturing agent to capture APRIL, or a complex comprising APRIL.

For example, in a first test format an APRIL-binding receptor (such as BCMA or TACI) or a binding equivalent thereof, such as hAPRIL.01A (disclosed in WO2010/100056) or an analogue may be immobilized on a solid support and sample from a subject, for example serum, is applied to the solid support. After washing (to remove unbound materials, in particular unbound materials interfering with APRIL detection), APRIL-binding peptide is added to the solid support and the presence of the APRIL-binding peptide is detected e.g. by detecting label attached to the APRIL-binding peptide or, according to some embodiments, by adding a labeled antibody specific for a Fc-chain on the APRIL-binding peptide. The detection may be qualitative, semi-quantitative or quantitative. Quantitative detection is preferred. Methods and means for detecting labeled peptides, such as labeled antibodies are known to the skilled person. For example use may be made of horseradish-peroxidase conjugated antibodies that bind to the Fc-chain of the APRIL-binding antibody. The conversion of chromogenic substrates (e.g., TMB, DAB, ABTS) by the horseradish-peroxidase into coloured products is used as a measure of bound APRIL.

In an alternative diagnostic format the diagnostic test is for detecting in a sample from a subject the amount of APRIL in complex with an APRIL receptor equivalent, such as hAPRIL.01A or an analogue thereof, administered to the subject. In this format the test may comprise:

providing the APRIL-binding peptide immobilized on a solid support;
applying the sample to the solid support and incubating to allow complex present in the sample to bind to the solid support;
washing;
detecting bound complex and/or detecting bound uncomplexed APRIL.

This test format for example is of value for determining the saturation of APRIL in the subject's serum with blockers of the APRIL-APRIL receptor interaction. For this it is preferred to detect both bound complex and detecting bound uncomplexed APRIL. This may be accomplished by detecting complexed and uncomplexed APRIL in separate incubations and/or by using different labels when targeting bound complex and bound uncomplexed APRIL. Uncomplexed APRIL may also be determined in the first test format presented above.

For detecting bound complexed and bound uncomplexed APRIL in the same incubation, complex may be targeted with a first detection peptide, such as an antibody, directed to the APRIL receptor equivalent, said first detection peptide bound to a first label, and uncomplexed APRIL may be targeted by a second detection peptide, such as an antibody, directed to APRIL, said second detection peptide bound to a second label, different from the first label. The second detection peptide may be selected such as to bind to the same region of APRIL as the APRIL receptor equivalent. Thus it may be selected as an APRIL receptor or an APRIL receptor equivalent. In fact in respect of its binding to APRIL it may be identical to the receptor equivalent administered to the subject. Thus the second detection peptide may differ only from the receptor equivalent, such as hAPRIL.01A or an analogue thereof, administered to the subject by having a label attached allowing detection discriminative from detection of the receptor equivalent administered to the subject. For example by containing a different Fc-chain. Within the present invention reference to hAPRIL.01A includes its analogues, in particular humanized analogues. It will be clear that the second detection peptide preferably should not bind to the same region of APRIL, where the selected APRIL-binding peptide binds to APRIL, nor should its binding to APRIL be disturbed by binding of the selected APRIL-binding peptide.

The test obtains a detection result, such as a detection value, for bound complex and/or bound uncomplexed APRIL. From the detection results the saturation level of APRIL with the administered APRIL-receptor equivalent may be determined, such that the therapeutic outcome of the treatment of the subject with the APRIL-receptor equivalent, such as hAPRIL.01A or an analogue thereof, may be assessed.

In embodiments of the diagnostic test of the invention, the APRIL-binding peptide or the APRIL-binding receptor (or a binding equivalent thereof) may be immobilized on for example the surface of a laboratory container, such as on the surface of micro-titer plate wells. It will be clear that by applying the sample to the solid support, the sample is applied to the immobilized April-binding peptide.

Washing is for removing unbound material, in particular unbound material interfering with APRIL detection, and may be achieved with any suitable washing liquid known to the skilled person. In general aqueous solutions will be used. Some general guidance in connection to washing liquids is also provided above in connection to the method for obtaining an APRIL-binding peptide.

It will be clear that in the diagnostic tests of the invention, reactions and processes such as applying the sample to the solid support and incubating to allow complex present in the sample to bind to the solid support, washing steps and detection steps may be preformed in a suitable container, such as a reaction vessel, in particular vessels used on laboratory scale for diagnostic purposes.

The above described exemplary diagnostic formats involve solid supports with immobilized peptides. It will be clear for the skilled person, that diagnostic test formats may also be executed completely in solution, for example by using Fluorescence Resonance Energy Transfer (FRET) methodologies, including Time Resolved FRET (TR-FRET or HTRF). The skilled person will know how to modify the test formats presented above in order to execute them completely in solution e.g. by using FRET methodologies. Also in test formats completely executed in solution, the APRIL-binding peptides of the invention are of use, as they may be used as an indicator for the presence of APRIL.

The skilled person will understand that in the various test formats, the reduced interference of the APRIL-binding peptides with the APRIL-APRIL receptor interaction is beneficial. It should be emphasized however, that the diagnostic use of the peptides of the invention is not limited to these exemplary test formats. The potential of the APRIL-binding peptides of the present invention for use in diagnostic and analytical applications is further supported by the results presented in the experimental section.

The APRIL-binding peptides of the present invention may also be employed in any other known assay method, such as competitive binding assays, direct and indirect sandwich assays, and immunoprecipitation assays (Zola, Monoclonal Antibodies. A Manual of Techniques, pp. 147-158 (CRC Press, Inc. 1987)).

The APRIL-binding peptides of the invention may also be used for in vivo diagnostic assays. Generally, the APRIL-binding peptide is labeled with a radionuclide so that an APRIL antigen or cells expressing it can be localized using immunoscintigraphy or positron emission tomography.

The APRIL-binding peptides of the invention may also have other, non-therapeutic uses. The non-therapeutic uses for the APRIL-binding peptides include flow cytometry, western blotting, enzyme linked immunosorbant assay (ELISA) and immunohistochemistry.

APRIL-binding peptides of this invention may for example also be used as an affinity purification reagent via immobilization to a Protein A-Sepharose column.

The invention will be further illustrated with reference to the following examples, which present non-limiting embodiments of the invention.

EXAMPLES

Example 1

Commercially Available APRIL Detection Assays do not Reliably Detect APRIL in Human Serum (HS)

To detect APRIL in serum of patients, an ELISA-based assays has been described that depends on capture of APRIL by human BCMA and detection of the bound antibody using a polyclonal rabbit APRIL-specific antibody (Planelles L et al., *Haematologica* 2007, 92:1284-5). However, the polyclonal antibody is only limited available and cannot be reproducibly obtained. To solve this problem the commercially available anti-APRIL assays were compared with the detection observed with the polyclonal antibody-based ELISA. For the polyclonal ELISA, plates were coated with 100 ng/well of BCMA-Fc (R&D systems) in Coating Buffer (0.2M Sodium Phosphate buffer, pH=6.5) at 4° C. After overnight coating, plates were washed three times with PBS plus 0.05% Tween 20 (PBST). Plates were then blocked at room temperature for an hour with PBS containing 10% human serum (assay diluent). For the commercial ELISA precoated plates were used (Biolegend, San Diego, USA). A standard curve was generated in assay diluent using recombinant human APRIL (R&D systems) or using the provided recombinant human APRIL (Biolegend). Subsequently human serum from colorectal cancer patients was diluted ten-fold in assay diluent and tested in both ELISAs in parallel. Detection of the bound APRIL was then performed either according to the manufacturer's instructions (Biolegend) with the provided monoclonal antibody coupled to horse radish peroxidase or with the polyclonal antibodies followed by a second step using goat-anti-rabbit peroxidase (1:1,000 in assay diluent). Antibody incubation steps were all for one hour in assay diluent at room temperature and followed by three washes with PBS/0.05% Tween 20.

As presented in FIG. 1, the commercially available APRIL ELISA does not reproduce the assay results based on the polyclonal antibody. In several cases high detection was observed with the polyclonal ELISA, which is not matched with high expression in the Biolegend ELISA. Reciprocally, several cases show clear detection in the Biolegend ELISA, while no APRIL is detected in the polyclonal ELISA. A correlation analysis using the Spearman R-value indicates a very low correlation of 0.5946 with a relative poor confidence interval. The ELISA therefore does not provide comparable data.

Figure 2A:
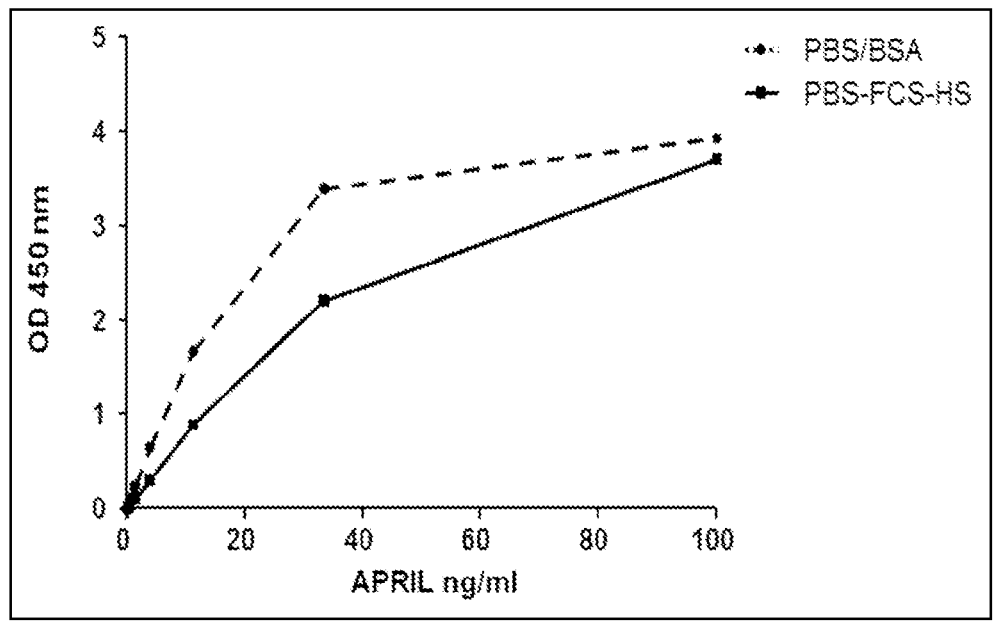
FIG. 2A-2D.

In addition, the effect of addition of human serum to APRIL was determined to analyse the effect of human serum on the quantification of APRIL. Two standard curves were generated using recombinant APRIL, which is produced by transfecting a construct that expresses APRIL wt into 293T cells. This recombinant APRIL is either diluted in PBS+10% Foetal Calf Serum+20% human serum (HS) (Sigma, cat num H4522) or diluted in PBS/1% BSA, at the concentrations of 100, 33.3, 11.1, 3.7, 1.23, 0.41, 0.136 and 0.04 ng/ml. Binding of these two standard curves were tested on several commercially available antibodies or ELISA kits to determine the effect of serum addition to the quantification of APRIL. For the APRIL ELISA provided by Biolegend, Legend MAX ELISA Kit with PRE-coated Plates (cat number:439307), all reagents were brought to room temperature prior to use. Plates were washed 4 times with at least 300 µl of 1× Wash Buffer (given by manufacturer) per well and blot any residual buffer by firmly tapping the plate upside down on absorbent paper. Next, 100 µl of standard curve dilutions were added, plates were sealed with the Plate Sealer included in the kit and incubated at room temperature for 2 hours, while shaking at 200 rpm. After this step the plates were washed four times with 1× Wash Buffer. Next, 100 µl of Human APRIL/TNFSF13 Detection Antibody solution was added (given by manufacturer) to each well, plates were sealed and incubated at room temperature for 1 hour, while shaking at 200 rpm. After the incubation the plates were washed four times with 1× Wash Buffer. The primary antibody was recognized by addition of 100 µl of Avidin-HRP A solution (given by manufacturer) to each well, and incubated at room temperature for 30 minutes while shaking. Finally, the plates were washed five times with 1× Wash Buffer. Bound complexes were visualized by adding 100 µl of Substrate Solution F (given by manufacturer) to each well and incubation at room temperature for 15 minutes in the dark. The reaction was stopped by adding 100 µl of Stop Solution (given by manufacturer) to each well. Absorbance was read at 450 nm. FIG. 2A presents the reduced APRIL detection in this assay in the presence of human serum.

Figure 2B:
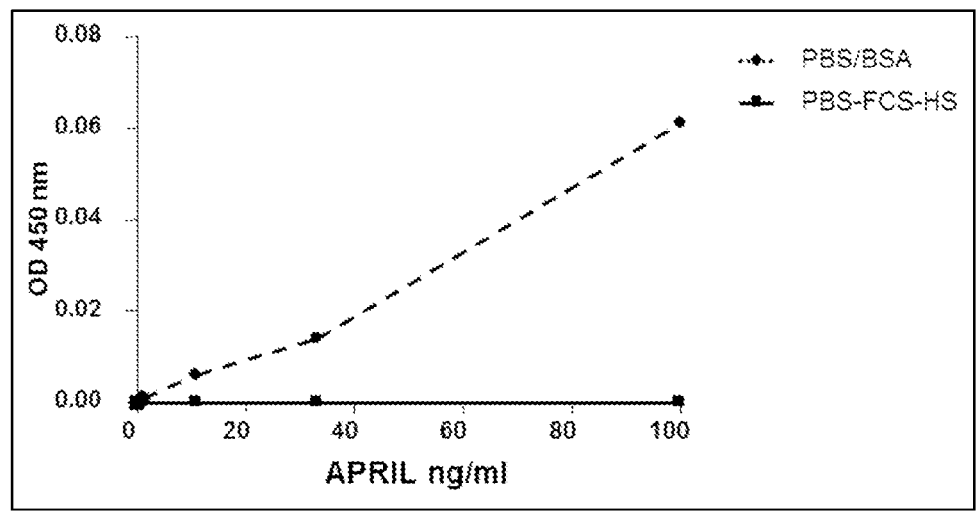

In analogy with the polyclonal antibody assay as described above, the detection of APRIL using a commercially available monoclonal antibody after capture by BCMA-Fc was evaluated. In FIG. 2B, the effect of human serum on the detection of APRIL is presented using APRILY-5 as a detection monoclonal antibody. ELISA plates were coated with 100 µl of 0.5 µg/ml BCMA-Fc (EBC0512081; R&D) in Coating Buffer (see above) and incubated overnight at 4° C. Plates were washed three times with PBS/0.2% Tween (previously described) and blocked to using 150 µl PBS/1% BSA for one hour at 37° C. After three times washing with PBS/0.2% Tween, 100 µl of the different standard curves were added into each well. Standard curve concentrations were incubated for 2 hr at room temperature. After the incubation time the plates were washed three times with PBS/0.2% Tween. Next, the commercially available APRILY-5 biotinylated (ALX-804-801-C100, Enzo Life Sciences BVBA, Antwerpen, Belgium) was added to the plates in 100 µl of 1 µg/ml diluted in PBS/1% BSA, this was done for one hour at 37° C. Next, plates were washed three times with PBS/0.2% Tween. The following step included the addition of a 100 µl of Streptavidin-HRP (cat. number 890803, R&D, UK) diluted 1:1,000 in PBS/1% BSA for one hour at 37° C. Plates were washed three times with PBS/0.2% Tween and bound immune complexes were visualized using 100 µl of TMB substrate. Reactions were stopped with 100 µl 0.5 M $H_2SO_4$ and absorbances were read at 450 nm. No APRIL was detected in the presence of human serum.

Figure 2C:
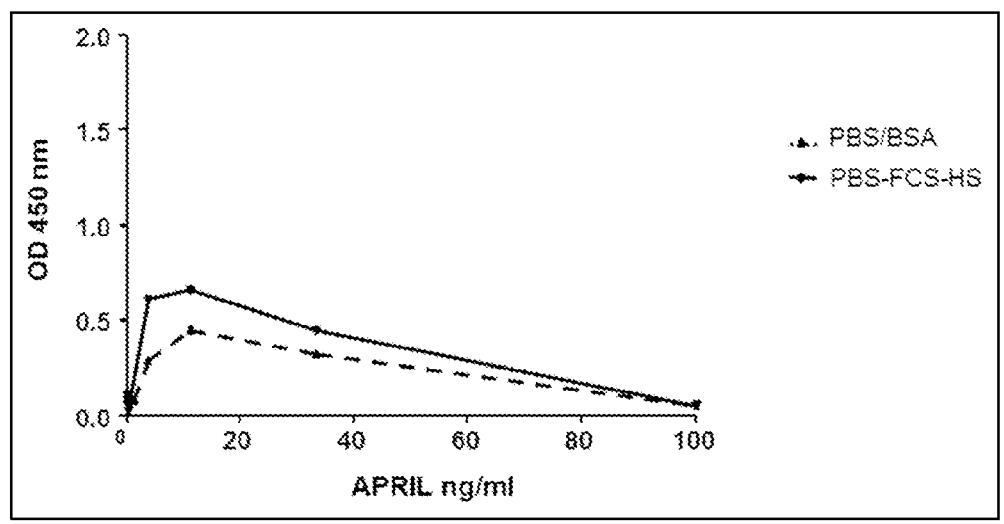

In FIG. 2C, the effect of human serum on the quantification of APRIL was determined using an ELISA assay that used the commercially available Sascha-2 anti-APRIL antibody to capture APRIL and using APRILY-5 bio antibody to detect bound APRIL. In this assay, ELISA plates were coated with 100 µl of anti-APRIL antibody Sascha-2 (804-804-C100, Enzo Life Sciences BVBA, Antwerpen, Belgium) in Coating buffer (see above) and incubated overnight at 4° C. Plates were washed three times with PBS/0.2% Tween and blocked with 150 µl PBS/1% BSA for one hour at 37° C. After washing three times with PBS/0.2% Tween, 100 µl of standard curve were incubated. 100 µl of these standard curves were added into each well, standard curve concentrations are incubated for two hours at room temperature. After incubation plates were washed three times with PBS/0.2% Tween. Next, the commercially available APRILY-5 biotinylated was added to the plates in 100 μl of 1 μg/ml diluted in PBS/1% BSA for one hour at 37° C. Next, the plates were washed three times with PBS/0.2% Tween. The following step included the addition of a 100 μl of Streptavidin-HRP diluted 1:1,000 in PBS/1% BSA for one hour at 37° C. Plates were washed 3 times with PBS/0.2% Tween and bound immune complexes were visualized by addition of 100 μl of TMB substrate. Reactions were stopped with 100 μl 0.5 M $H_2SO_4$ and absorbances were read at 450. No reliable detection of APRIL was observed either in the absence or presence of human serum.

Figure 2D:
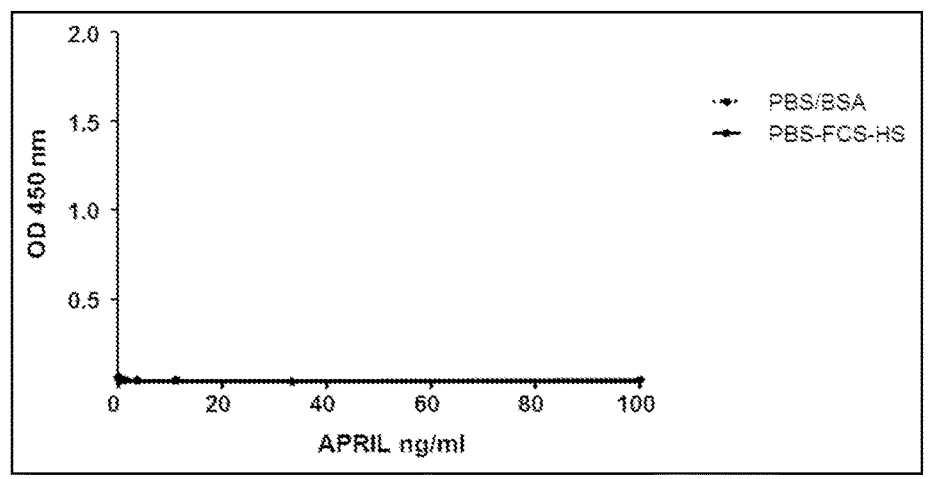

Finally, in FIG. 2D we assessed the use of a second commercially available APRIL ELISA, the Duo Set ELISA anti human APRIL/TNFSF13, (cat num DY884) from R&D Systems. Plates were coated by diluting the Capture Antibody (given by manufacturer, 843362) to a final concentration of 2 μg/ml diluted in PBS. 96-well plates were coated with 100 μl per well and incubated overnight at room temperature. The day after, plates were washed four times with Wash Buffer (given by manufacturer, cat num WA126). Plates were blocked by adding 300 μl of Reagent Diluent to each well (given by manufacturer, cat num DY995) and incubated at room temperature for 1 hour. Afterwards, plates were washed four times. Later, 100 μl of standard curves or serum samples were added. The serum samples were diluted five times in reagent diluent, covered with an adhesive strip and incubated for 2 hours at room temperature. Next, plates were washed four times and APRIL in serum was detected using 100 μl of the Detection Antibody (given by manufacturer, cat num 843363) diluted in Reagent Diluent, to each well and incubated 2 hours at room temperature. Plates were washed four times. Afterwards, 100 μl of the working dilution of Streptavidin-HRP (cat num 890803, R&D, UK) were added to each well, plates were covered and incubated for 20 minutes at room temperature. Plates were washed four times. Immune complexes were visualized by addition of 100 μl of Substrate Solution to each well (given by manufacturer, DY999) and incubated for 20 minutes at room temperature. The reaction was stopped by addition of 50 μl of Stop Solution to each well (DY994). Bound APRIL was detected by optical density at 450 nm. No APRIL was detected.

Taken together, none of the commercially available ELISA assays or monoclonal anti-APRIL antibodies reproduced the assay results obtained using the polyclonal antibodies as described above and all demonstrated a large interference of human serum in the quantification of human APRIL.

Example 2

Immunization and Selection of Anti-APRIL Antibodies
Immunization of Mice with APRIL cDNA To isolate antibodies against the human APRIL protein that allow detection of APRIL in the context of human serum, mice were immunized with hAPRIL cDNA. Next, selection procedures were designed and developed to specifically isolate B-cells expressing anti-hAPRIL antibodies that bind to human APRIL in binding interaction with BCMA.

Anti-hAPRIL antibodies were raised by cDNA immunization of mice. First, the cDNA encoding the full length open reading frame of hAPRIL was subcloned into the pCI-neo vector (Promega, Madison, Wis.). Expression of the obtained vector was checked by transient transfection of pCI-neo-hAPRIL in 293 cells (American Type Culture Collection, Manassas, Va.) and immunoblotting with mouse anti-hAPRIL IgG1 Aprily-5 (1:5,000) (Alexis, San Diego, Calif.), followed by goat anti-mouse IgG1-HRP (1:2,000) (Southern Biotechnology, Birmingham, Ala.). Mice were immunized by gene gun immunization using a Helios Gene gun (BioRad, Hercules, Calif.) and DNA coated gold bullets (BioRad) following manufacturer's instructions. Briefly, 1 μm gold particles were coated with pCI-neo-hAPRIL cDNA and commercial expression vectors for mouse Flt3L and mouse GM-CSF in a 2:1:1 ratio (both from Aldevron, Fargo, N. Dak.). A total of 1 μg of plasmid DNA was used to coat 500 μg of gold particles.

Specifically, 7-8 weeks old female BALB/C mice were immunized in the ears with a gene gun, receiving 3 cycles of a shot in both ears. Approximately, a 1:800-2,400 anti-hAPRIL titer was detected by ELISA in mouse serum after three DNA immunizations. In the ELISA, all incubation steps were followed by a wash step with PBST (PBS with 0.01% Tween 20). Maxisorp 96-well immunoplates (Nunc, Rochester, N.Y.) were coated with rabbit anti-FLAG polyclonal antibody (50 ng/well in PBS) (Sigma, F7425) overnight at 4° C. and blocked with 10% Goat serum/PBST for 1 hour at RT. Plates were incubated with supernatant (1:10 in PBS) from 293T cells transiently transfected with CMV promoter driven secreted form of FLAG-hAPRIL (pCR3-hAPRIL) for 1 h at RT, followed by incubations with mouse sera dilutions and 1:2,000 HRP-conjugated goat anti-mouse IgG (Southern Biotechnology) for 1 hour each at RT. After the final PBST wash, anti-hAPRIL immunoreactivity was visualized with 100 μl stabilized chromagen (Invitrogen, SB02). Reactions were stopped with 100 μl 0.5 M $H_2SO_4$ and absorbances were read at 450 and 620 nm. Mice that demonstrated reactivity against hAPRIL were immunized for a final, third time and sacrificed four days later.

Erythrocyte-depleted spleen and lymph-node cell populations were prepared as described previously (Steenbakkers et al., 1992, *J. Immunol. Meth.* 152: 69-77; Steenbakkers et al., 1994, *Mol. Biol. Rep.* 19: 125-134) and frozen at −140° C.

Selection of Anti-APRIL Antibody Producing B Cells

Figure 3:
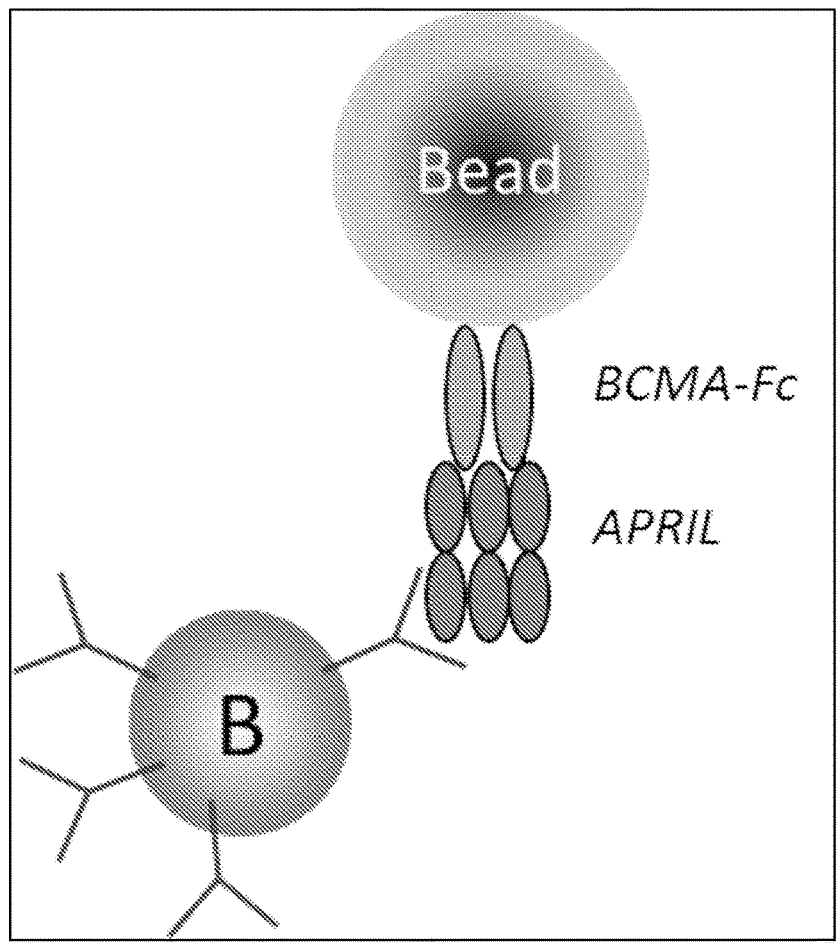
FIG. 3. Selection strategy to identify APRIL-binding peptides that allow detection in serum. Magnetic DynaBeads were loaded with BCMA-Fc recombinant protein, which after extensive washing was allowed to bind recombinant FLAG-APRIL.

To specifically select anti-hAPRIL antibody producing B-cells that detect APRIL in the presence of human serum, a selection strategy was designed and developed that preferentially bound B-cells that express anti-hAPRIL antibodies that bind APRIL when in binding interaction with BCMA-Fc (FIG. 3). $4×10^7$ M-450 Tosyl activated magnetic Dynabeads (Cat 140.13) were incubated over weekend at 4° C. with 20 μg recombinant BCMA-Fc (R&D systems, cat #193-13C) in 0.1 M Phosphate buffer, pH 7.4. Next, the supernatant was aspirated and beads were blocked with PBS/1% BSA by incubation for one hour at 4° C. Next, beads were washed 3 times with PBS/0.1% BSA. Subsequently, beads were incubated with FLAG-APRIL containing supernatant (1:10 in PBS, from 293T cells transiently transfected with CMV promoter driven secreted form of FLAG-hAPRIL (pCR3-hAPRIL)) by incubation for one hour at 4° C. Finally, beads were resuspended in PBS/0.1% BSA.

To select B cell clones producing reduced-blocking anti-hAPRIL antibodies, $1.4×10^7$ erythrocyte-depleted splenocytes were thawn. hAPRIL-specific B-cells were selected by subjecting the splenocytes to selection on APRIL-BCMA complexed tosyl-activated magnetic DynaBeads in a beads: cells ratio of 1:1.5. Aspecific binding splenocytes were washed away by 15× washes with 5 ml of DMEM F12/P/S/10% BCS medium. Next, selected B-cells were cultured as described by Steenbakkers et al., 1994, *Mol. Biol. Rep.* 19: 125-134. Briefly, selected B-cells were mixed with 7.5% (v/v) T-cell supernatant and 50,000 irradiated (2,500 RAD) EL-4 B5 nursing cells in a final volume of 200 µl DMEM F12/P/S/10% BCS in a 96-well flat-bottom tissue culture plates.

On day nine, supernatants were screened for hAPRIL reactivity by ELISA. In the ELISA, all incubation steps were followed by a wash step with PBST (PBS with 0.01% Tween 20). Maxisorp 96-well immunoplates (Nunc, Rochester, N.Y.) were coated with 0.2 µg/ml BCMA-Fc (R&D Systems, 193-13C) in PBS, (50 µl/well in PBS) overnight at 4° C. and blocked with PBS/1% BSA for 1 hour at RT. Plates were incubated with supernatant (1:10 in PBS) from 293T cells transiently transfected with CMV promoter driven secreted form of FLAG-hAPRIL (pCR3-hAPRIL) for 1 h at RT, followed by incubations with 50 µl supernatant from the B-cell cultures and 1:5,000 HRP-conjugated goat anti-mouse IgG (Southern Biotechnology) for 1 hour each at RT. After the final PBST wash, anti-hAPRIL immunoreactivity was visualized with 100 µl Stabilized chromagen (Invitrogen, SB02). Reactions were stopped with 100 µl 0.5 M $H_2SO_4$ and absorbances were read at 450 nM. B-cell clones expressing hAPRIL-reactive antibodies were identified by ELISA.

Subsequently, B-cell clones from the hAPRIL reactive supernatants were immortalized by mini-electrofusion following published procedures (Steenbakkers et al., 1992, J. Immunol. Meth. 152: 69-77; Steenbakkers et al., 1994, Mol. Biol. Rep. 19:125-34). Specifically, B-cells were mixed with $10^6$ Sp2/0-Ag14 myeloma cells, and serum was removed by washing with DMEM F12 media. Cells were treated with Pronase solution (Calbiochem, cat. no. 4308070.536) for 3 minutes and washed with Electrofusion Isomolar Buffer (Eppendorf, cat. no. 53702). Electrofusions were performed in a 50 µl fusion chamber by an alternating electric field of 30 s, 2 MHz, 400 V/cm followed by a square, high field pulse of 10 µs, 3 kV/cm and again by an alternating electric field of 30 s, 2 MHz, 400 V/cm.

Contents of the chamber were transferred to hybridoma selective medium and plated in a 96-well plate under limiting dilution conditions. On day 12 following the fusions, hybridoma supernatants were screened for hAPRIL-binding activity, as described above. Five hybridomas that secreted antibodies in the supernatant that recognized hAPRIL were subcloned by limited dilution to safeguard their integrity. The following anti-hAPRIL antibodies were selected for further analysis: hAPRIL.130, hAPRIL.132, hAPRIL.133, hAPRIL.135, hAPRIL.138.

The selection strategy used to identify the APRIL-binding peptides (here an immunoglobulin expressed on a B-cell (B)) is schematically presented in FIG. 3. In this schematic figure BCMA-Fc (acting as shielding peptide) is bound (or other wise immobilized) to the solid support (Bead) and the target peptide (APRIL) is immobilized on the solid support by the interaction with BCMA. However, as is clear from the description above, in alternative embodiments the target peptide may be bound (or other wise immobilized) to the solid support and the shielding peptide may be immobilized on the solid support by its interaction with the target peptide.

Example 3

Purification and Characterization of Anti-APRIL Antibodies Stabilization of Anti-APRIL Producing Hybridomas and Purification of Anti-APRIL Antibodies Clonal cell populations were obtained for the hAPRIL hybridomas by two rounds of limiting dilutions. Stable hybridomas were cultured in serum-free media for 7-10 days; supernatants were harvested and filtered through a 0.22 µM nitrocellulose membrane. Antibodies were purified using mAb Select SuRe ProtA resin according to the manufacturer's instructions (GE Healthcare, cat. no.17-5438). Buffer was exchanged for PBS using PD-10 gel-filtration columns (GE Healthcare). Antibodies were quantified using spectrophotometry. Using a mouse monoclonal antibody isotyping test kit (Roche, #11493027001), the (sub)-isotype of all hAPRIL antibodies was determined to be IgG1, Kappa.

Cloning of Immunoglobulin cDNAs

Degenerate primer PCR-based methods were used to determine the DNA sequences encoding the variable regions for the mouse antibody that is expressed by the hAPRIL hybridoma's: hAPRIL.130, hAPRIL.132, hAPRIL.133, hAPRIL.135 and hAPRIL.138.

Total RNA was isolated from about $5\times10^6$ hybridoma cells using RNeasy mini kit (Qiagen, 74106) according to manufacturer's instructions and treated with Deoxyribonuclease I (Invitrogen) according to the manufacturer's instructions. Gene specific cDNAs for the heavy and light chains were synthesized using the M-MLV Reverse Transcriptase, RNase H Minus, point mutant kit (Promega, cat. no. M3683) according to the manufacturer's instructions. The $V_H$ and $V_L$ genes were PCR-amplified using a Novagen-based Ig-primer set (Novagen, San Diego, Calif.) and Accuprime Pfx DNA polymerase (Invitrogen). All PCR products that matched the expected amplicon size of 500 bp were cloned into pCR4 TOPO vector (Invitrogen), and the constructs were transformed in Subcloning efficient DH5a competent cells (Invitrogen) according to the manufacturer's instructions.

Clones were screened by colony PCR using universal M13 forward and reverse primers, and at least two clones from each reaction were selected for DNA sequencing analysis. CDRs were identified following the Kabat rules (Kabat et al., 1991. *Sequences of Proteins of Immunological Interest*, Fifth Edition, NIH Publication No. 91-3242).

The sequences are disclosed in the attached Sequence Listing and listed in Table 1 above.

Example 4

Anti-APRIL Antibodies Detect APRIL in Human Serum and Transgenic Mice

Figure 4A:
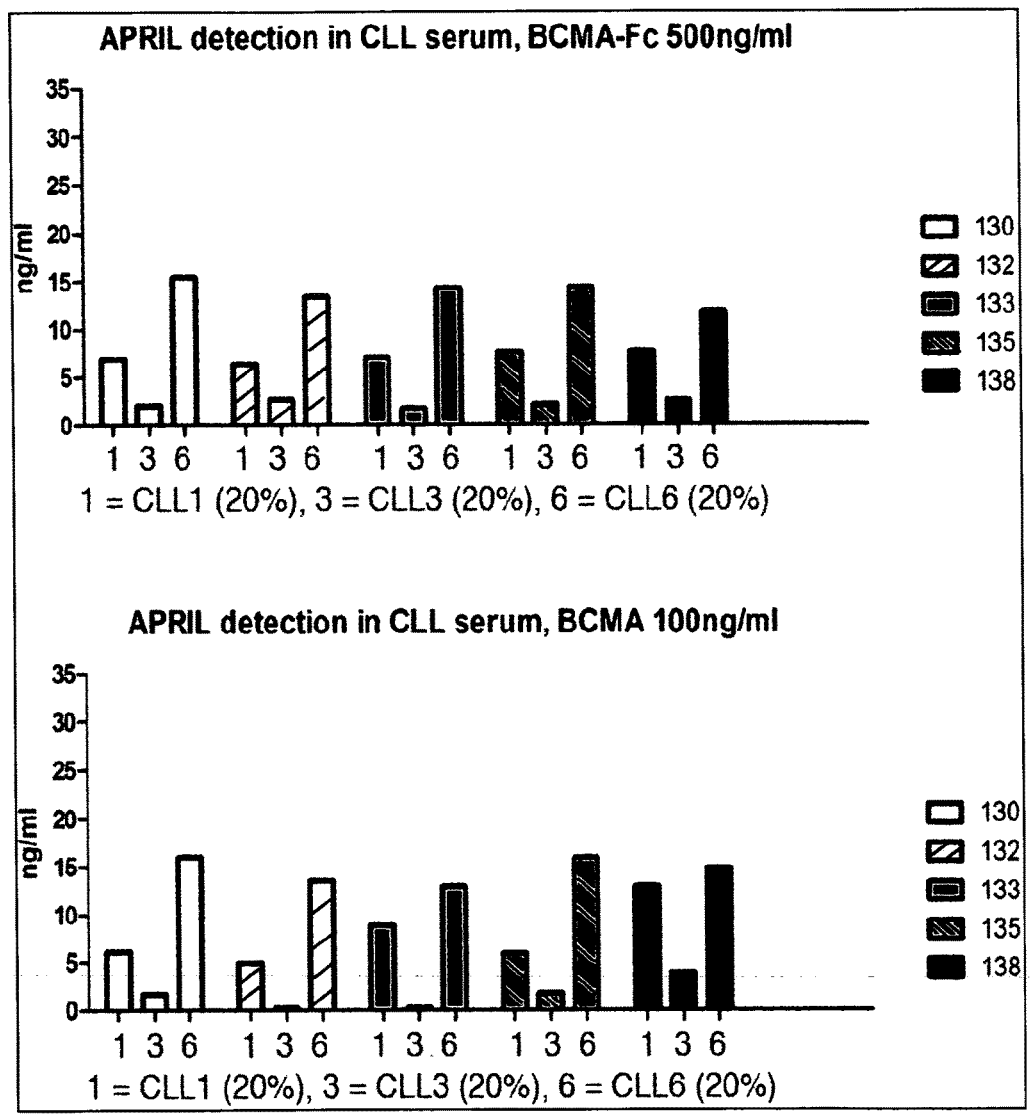
FIG. 4A and 4B.

To quantify the APRIL serum levels in serum derived from CLL patients using the newly identified APRIL monoclonal antibodies, hAPRIL.130, hAPRIL.132, hAPRIL.133, hAPRIL.135 and hAPRIL.138 the following ELISA assay was performed. ELISA plates were coated with 100 µl of 0.5 µg/ml BCMA-Fc (EBC0512081; R&D), in coating buffer (0.2 M Sodium Phosphate, pH=6.5) and incubated overnight at 4° C. Next, plates were washed three times with PBS/ 0.2% Tween and blocked with 150 µl PBS/1% BSA for one hour at 37° C. After washing 3 times with PBS/0.2% Tween 100 µl of samples or standard curves was added. The CLL serum samples were five times diluted in PBS/10% FCS, while standard curve was diluted in PBS+FCS 10%+HS 20%. Samples and standard curve concentrations were incubated for 2 hr at room temperature. Next, plates were washed three times with PBS/0.2% Tween. Next, 100 µl of the anti-APRIL monoclonal antibody was added to the plates at a concentration of 1 µg/ml diluted in PBS/1% BSA and incubated for one hour at 37° C. Subsequently, plates were washed three times with PBS/0.2% Tween and 100 µl of Goat anti-Mouse IgG (H&L) (Southern Biotech, cat number 1031-05), diluted 1:1,000 in PBS/1% BSA was added and incubated for one hour at 37° C. Plates were washed three times with PBS/0.2% Tween and bound immune complexes visualized by addition of 100 µl of TMB substrate (TMB). The reaction was stopped by adding an equal amount of 1 M hydrochloric acid to the reaction volume. Bound APRIL was quantified by measurement of optical density at 450 nm. As depicted in FIG. 4A, all monoclonal antibodies revealed APRIL in the serum of the patients to the same extent.

Figure 4B:
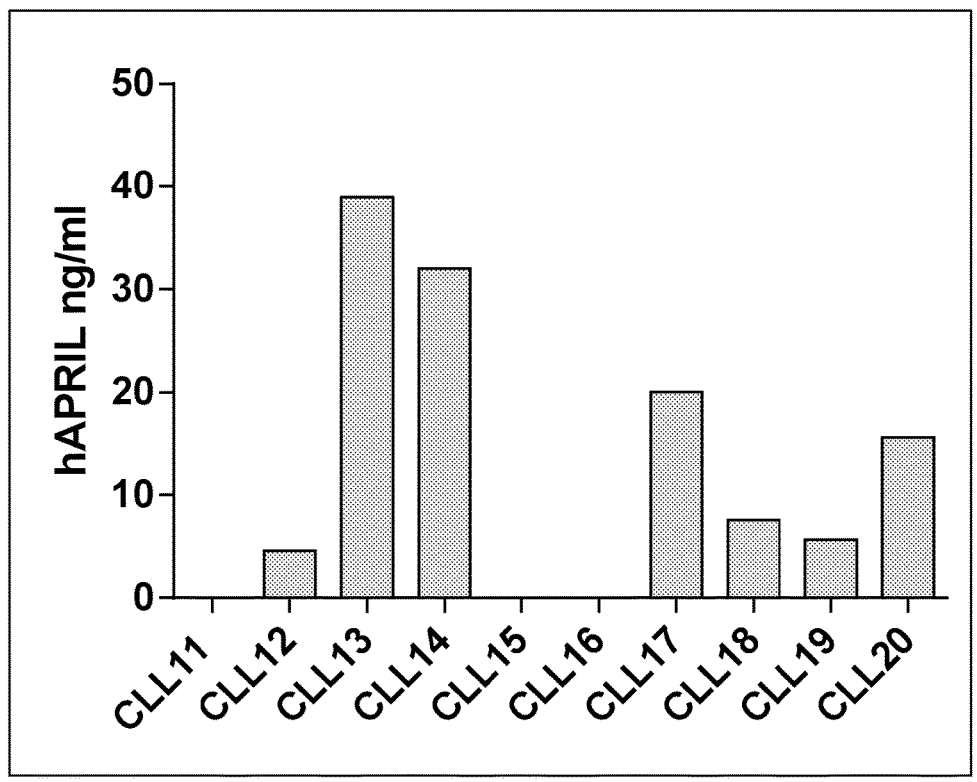

Next, using hAPRIL.133 monoclonal antibody the analysis was extended using the same ELISA set-up. Additional samples of 10 CLL patients with varying amounts of APRIL were analyzed (FIG. 4B).

Figure 5:
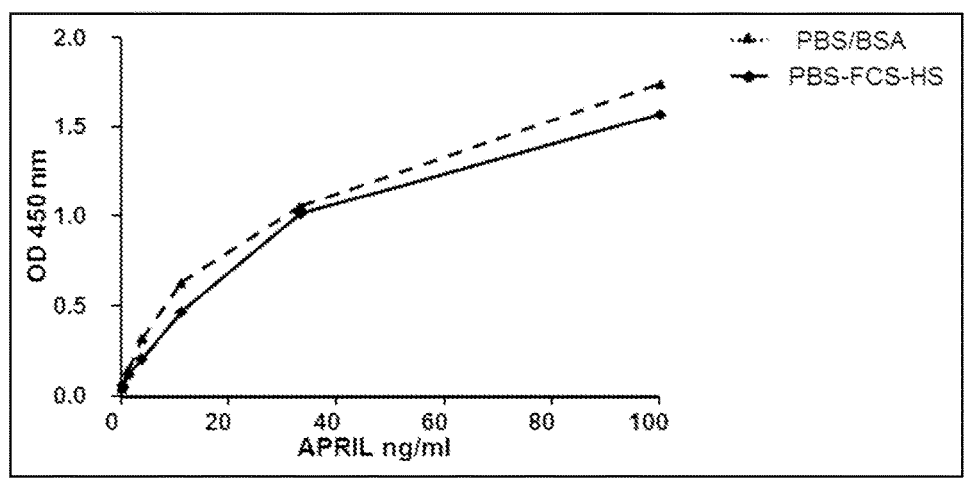
FIG. 5. APRIL quantification using BCMA-Fc and APRIL-binding peptide of the invention (hAPRIL.133 mAb) is not impacted by the presence of human serum. Two standard curves were generated using recombinant APRIL diluted in PBS+10% Foetal Calf Serum+20% human serum (HS) (referred to as PBS-FCS-HS) or diluted in PBS/1% BSA (referred to as PBS/BSA), at the concentrations of 100, 33.3, 11.1, 3.7, 1.23, 0.41, 0.136 and 0.04 ng/ml.

In addition, the effect of presence of human serum on the quantification of APRIL was studied using the assay format using BCMA-Fc capture and hAPRIL.133 antibody for detection. Two standard curves were generated using recombinant APRIL, which is produced transfecting a construct that expresses APRIL wt into 293T cells. This recombinant APRIL is either diluted in PBS+10% Foetal Calf Serum+ 20% human serum (HS) (Sigma, cat number H4522) or diluted in PBS/1% BSA, at the concentrations of 100, 33.3, 11.1, 3.7, 1.23, 0.41, 0.136 and 0.04 ng/ml. Binding of these two standard curves were established (FIG. 5). ELISA plates were coated with 100 µl of 0.5 µg/ml BCMA-Fc (EBC0512081; R&D), in coating buffer (0.2 M Sodium Phosphate, pH=6.5) and incubated overnight at 4° C. Next, plates were washed three times with PBS/0.2% Tween and blocked with 150 µl PBS/1% BSA for one hour at 37° C. After washing three times with PBS/0.2% Tween 100 µl standard curves was added. Standard curve concentrations were incubated for 2 hr at room temperature. Next, plates were washed 3 times with PBS/0.2% Tween. Next, 100 µl of the anti-hAPRIL.133 monoclonal antibody was added to the plates at a concentration of 1 µg/ml diluted in PBS/1% BSA and incubated for one hour at 37° C. Subsequently, plates were washed three times with PBS/0.2% Tween and 100 µl of Goat anti-Mouse IgG (H&L) (Southern Biotech, cat num 1031-05), diluted 1:1,000 in PBS/1% BSA was added and incubated for one hour at 37° C. Plates were washed three times with PBS/Tween 0.2% and bound immune complexes visualized by addition of 100 µl of TMB substrate (TMB). The reaction was stopped by adding an equal amount of 1 M hydrochloric acid to the reaction volume. Bound APRIL was quantified by measurement of OD at 450 nm. No effect of the presence of human serum is observed in this assay format using APRIL binding peptides obtained with the method of the invention.

The invention claimed is:

1. An A Proliferation-Inducing Ligand (APRIL)-binding peptide comprising immunoglobulin $V_H$ and $V_L$ domains, wherein the $V_H$ domain comprises an amino acid sequence having complementarity determining region sequences set forth in SEQ ID NO: 25, 26, 27 and at least 90% sequence similarity with SEQ ID NO: 23; and the $V_L$ domain comprises an amino acid sequence having complementarity determining region sequences set forth in SEQ ID NO: 28, 29, 30 and having at least 90% sequence similarity with SEQ ID NO: 24.

2. An APRIL-binding peptide according to claim 1, wherein the $V_H$ domain comprises an amino acid sequence having at least 95% sequence similarity with SEQ ID NO: 23; and the $V_L$ domain comprises an amino acid sequence having at least 95% sequence similarity with SEQ ID NO: 24.

3. An APRIL-binding peptide comprising immunoglobulin $V_H$ and $V_L$ domains, wherein the $V_H$ domain comprises the amino acid sequence of SEQ ID NO: 23; and the $V_L$ domain comprises the amino acid sequence of SEQ ID NO: 24.

* * * * *